(12) United States Patent
Efimov et al.

(10) Patent No.: US 10,099,062 B2
(45) Date of Patent: Oct. 16, 2018

(54) METHODS AND DEVICES FOR MULTI-STAGE VENTRICULAR THERAPY

(71) Applicant: The Washington University, St. Louis, MO (US)

(72) Inventors: Igor R. Efimov, Wildwood, MO (US); Wenwen Li, St. Louis, MO (US); Ajit H. Janardhan, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 15/367,927

(22) Filed: Dec. 2, 2016

(65) Prior Publication Data

US 2017/0080243 A1 Mar. 23, 2017

Related U.S. Application Data

(63) Continuation of application No. 14/524,712, filed on Oct. 27, 2014, now Pat. No. 9,526,907, which is a
(Continued)

(51) Int. Cl.
*A61B 17/3205* (2006.01)
*A61N 1/05* (2006.01)
(Continued)

(52) U.S. Cl.
CPC ......... *A61N 1/3906* (2013.01); *A61N 1/3918* (2013.01); *A61N 1/3956* (2013.01);
(Continued)

(58) Field of Classification Search
CPC ...... A61N 1/3956; A61N 1/39; A61B 5/0402; A61B 5/0464; A61B 5/7239
(Continued)

(56) References Cited

U.S. PATENT DOCUMENTS

| | | |
|---|---|---|
| 3,605,754 A | 9/1971 | Jaros et al. |
| 3,729,008 A | 4/1973 | Berkovits |

(Continued)

FOREIGN PATENT DOCUMENTS

| | | |
|---|---|---|
| EP | 0393265 A1 | 10/1990 |
| EP | 1062971 A1 | 12/2000 |

(Continued)

OTHER PUBLICATIONS

Bhandari et al., "Efficacy of Low-Energy T Wave Shocks for Induction of Ventricular Fibrillation in Patients with Implantable Cardioverter Defibrillators". Journal of Electrocardiology, vol. 31, No. 1, 1998, pp. 31-37.

(Continued)

*Primary Examiner* — Carl H Layno
*Assistant Examiner* — Jon Eric C Morales
(74) *Attorney, Agent, or Firm* — Patterson Thuente Pedersen, P.A.

(57) ABSTRACT

Methods and apparatus for a three-stage ventricular cardioversion and defibrillation therapy that treats ventricular tachycardia and fibrillation at low energy levels. An implantable therapy generator adapted to generate and selectively deliver a three-stage ventricular therapy and at least two leads operably each having at least one electrode adapted to be positioned proximate the ventricle of the patient. The device is programmed to deliver a three-stage therapy via both a far-field configuration and a near-field configuration of the electrodes upon detection of a ventricular arrhythmia. The three-stage therapy includes a first stage for unpinning of one or more singularities associated with the ventricular arrhythmia, a second stage for anti-repinning of the one or more singularities, both of which are delivered via the far-field configuration of the electrodes, and a third stage for (Continued)

extinguishing of the one or more singularities associated delivered via the near-field configuration of the electrodes.

52 Claims, 18 Drawing Sheets

Related U.S. Application Data continuation of application No. 13/349,527, filed on Jan. 12, 2012, now Pat. No. 8,874,208, which is a continuation-in-part of application No. 12/776,196, filed on May 7, 2010, now Pat. No. 8,560,066, which is a continuation-in-part of application No. 12/333,257, filed on Dec. 11, 2008, now Pat. No. 8,509,889.

(60) Provisional application No. 61/012,861, filed on Dec. 11, 2007.

(51) Int. Cl.
*A61N 1/39* (2006.01)
*A61N 1/362* (2006.01)

(52) U.S. Cl.
CPC .......... *A61N 1/3981* (2013.01); *A61N 1/3624* (2013.01); *A61N 1/395* (2013.01)

(58) Field of Classification Search
USPC ........................................................ 607/5, 9
See application file for complete search history.

(56) References Cited

U.S. PATENT DOCUMENTS

| | | |
|---|---|---|
| 3,738,370 A | 6/1973 | Charms |
| 3,942,536 A | 3/1976 | Mirowski et al. |
| 4,136,703 A | 1/1979 | Wittkampf |
| 4,384,585 A | 5/1983 | Zipes |
| 4,708,145 A | 11/1987 | Tacker, Jr. et al. |
| 4,727,877 A | 3/1988 | Kallok |
| 5,107,834 A | 4/1992 | Ideker et al. |
| 5,199,429 A | 4/1993 | Kroll et al. |
| 5,265,600 A | 11/1993 | Adams et al. |
| 5,275,621 A | 1/1994 | Mehra |
| 5,282,836 A | 2/1994 | Kreyenhagen et al. |
| 5,306,291 A | 4/1994 | Kroll et al. |
| 5,330,509 A | 7/1994 | Kroll et al. |
| 5,334,219 A | 8/1994 | Kroll |
| 5,365,391 A | 11/1994 | Sugiyama et al. |
| 5,372,605 A | 12/1994 | Adams et al. |
| 5,383,907 A | 1/1995 | Kroll |
| 5,387,613 A | 2/1995 | Goldberg et al. |
| 5,391,186 A | 2/1995 | Kroll et al. |
| 5,403,356 A | 4/1995 | Hill et al. |
| 5,405,363 A | 4/1995 | Kroll |
| 5,407,444 A | 4/1995 | Kroll |
| 5,413,591 A | 5/1995 | Kroll |
| 5,433,729 A | 7/1995 | Adams et al. |
| 5,489,293 A | 2/1996 | Pless et al. |
| 5,545,182 A | 8/1996 | Stotts et al. |
| 5,545,204 A | 8/1996 | Cammilli et al. |
| 5,562,708 A | 10/1996 | Combs et al. |
| 5,620,464 A | 4/1997 | Kroll et al. |
| 5,620,468 A | 4/1997 | Mongeon et al. |
| 5,674,248 A | 10/1997 | Kroll et al. |
| 5,676,687 A | 10/1997 | Ayers |
| 5,683,429 A | 11/1997 | Mehra |
| 5,766,226 A | 6/1998 | Pedersen |
| 5,792,187 A | 8/1998 | Adams |
| 5,797,967 A | 8/1998 | KenKnight |
| 5,813,999 A | 9/1998 | Ayers et al. |
| 5,840,079 A | 11/1998 | Warman et al. |
| 5,925,066 A | 7/1999 | Kroll et al. |
| 5,928,270 A | 7/1999 | Ramsey, III |
| 5,995,871 A | 11/1999 | Knisley |
| 6,070,081 A | 5/2000 | Takahashi et al. |
| 6,081,746 A | 6/2000 | Pendekanti et al. |
| 6,085,116 A | 7/2000 | Pendekanti et al. |
| 6,085,119 A | 7/2000 | Scheiner et al. |
| 6,091,991 A | 7/2000 | Warren |
| 6,094,596 A | 7/2000 | Morgan |
| 6,141,588 A | 10/2000 | Cox et al. |
| 6,157,859 A | 12/2000 | Alt |
| 6,178,351 B1 | 1/2001 | Mower |
| 6,185,459 B1 | 2/2001 | Mehra et al. |
| 6,205,357 B1 | 3/2001 | Ideker et al. |
| 6,233,483 B1 | 5/2001 | Causey, III et al. |
| 6,246,906 B1 | 6/2001 | Hsu et al. |
| 6,292,691 B1 | 9/2001 | Pendekanti et al. |
| 6,327,500 B1 | 12/2001 | Cooper et al. |
| 6,463,330 B1 | 10/2002 | Rabinovitch et al. |
| 6,510,342 B1 | 1/2003 | Park et al. |
| 6,526,317 B2 | 2/2003 | Hsu et al. |
| 6,556,862 B2 | 4/2003 | Hsu et al. |
| 6,567,698 B2 | 5/2003 | Herleikson |
| 6,587,720 B2 | 7/2003 | Hsu et al. |
| 6,711,442 B1 | 3/2004 | Swerdlow et al. |
| 6,745,081 B1 | 6/2004 | Helland et al. |
| 6,754,525 B1 | 6/2004 | Province et al. |
| 6,763,266 B1 | 7/2004 | Kroll |
| 6,813,516 B2 | 11/2004 | Ujhelyi et al. |
| 6,847,842 B1 | 1/2005 | Rodenhiser et al. |
| 6,937,896 B1 | 8/2005 | Kroll |
| 7,006,867 B1 | 2/2006 | Kroll |
| 7,020,517 B2 | 3/2006 | Weiner |
| 7,047,071 B2 | 5/2006 | Wagner et al. |
| 7,079,891 B1 | 7/2006 | Kroll |
| 7,110,811 B2 | 9/2006 | Wagner et al. |
| 7,113,822 B1 | 9/2006 | Kroll |
| 7,120,490 B2 | 10/2006 | Chen et al. |
| 7,127,292 B2 | 10/2006 | Warman et al. |
| 7,139,611 B1 | 11/2006 | Kroll et al. |
| 7,142,927 B2 | 11/2006 | Benser et al. |
| 7,142,928 B2 | 11/2006 | Sharma et al. |
| 7,155,286 B1 | 12/2006 | Kroll et al. |
| 7,181,276 B1 | 2/2007 | Province et al. |
| 7,480,351 B2 | 1/2009 | Hiatt, Jr. et al. |
| 7,532,933 B2 | 5/2009 | Hastings et al. |
| 7,647,109 B2 | 1/2010 | Hastings et al. |
| 7,848,823 B2 | 12/2010 | Drasler et al. |
| 7,899,537 B1 | 3/2011 | Kroll et al. |
| 7,925,343 B1 | 4/2011 | Min et al. |
| 8,032,218 B2 | 10/2011 | Wong et al. |
| 8,175,702 B2 | 5/2012 | Efimov et al. |
| 8,204,605 B2 | 6/2012 | Hastings et al. |
| 8,509,889 B2 | 8/2013 | Efimov et al. |
| 8,560,066 B2 * | 10/2013 | Efimov ................. A61N 1/395 607/5 |
| 8,639,325 B2 | 1/2014 | Efimov et al. |
| 8,706,216 B2 * | 4/2014 | Efimov ................. A61N 1/395 607/5 |
| 8,874,208 B2 * | 10/2014 | Efimov ................. A61N 1/3981 607/14 |
| 9,067,079 B2 | 6/2015 | Efimov et al. |
| 9,289,620 B2 | 3/2016 | Efimov et al. |
| 9,526,907 B2 | 12/2016 | Efimov et al. |
| 9,586,055 B2 | 3/2017 | Efimov et al. |
| 2001/0014816 A1 | 8/2001 | Hsu et al. |
| 2002/0128565 A1 | 9/2002 | Rudy |
| 2003/0083727 A1 | 5/2003 | Casavant et al. |
| 2003/0130703 A1 | 7/2003 | Florio et al. |
| 2003/0220676 A1 | 11/2003 | Helland |
| 2004/0102811 A1 | 5/2004 | Schwartz et al. |
| 2004/0111123 A1 | 6/2004 | Ware et al. |
| 2005/0096701 A1 | 5/2005 | Donovan et al. |
| 2005/0154420 A1 | 7/2005 | Diaz et al. |
| 2006/0161206 A1 | 7/2006 | Efimov et al. |
| 2007/0021793 A1 | 1/2007 | Voegele et al. |
| 2007/0088395 A1 | 4/2007 | Province et al. |
| 2009/0062877 A1 | 3/2009 | Krinski et al. |
| 2009/0204164 A1 | 8/2009 | Efimov et al. |
| 2010/0016917 A1 | 1/2010 | Efimov et al. |
| 2011/0009916 A1 | 1/2011 | Efimov et al. |
| 2011/0029032 A1 | 2/2011 | Bardy et al. |

(56) References Cited

U.S. PATENT DOCUMENTS

| | | |
|---|---|---|
| 2012/0203297 A1 | 8/2012 | Efimov et al. |
| 2012/0209343 A1 | 8/2012 | Efimov et al. |
| 2013/0013012 A1 | 1/2013 | Efimov et al. |
| 2015/0045847 A1 | 2/2015 | Efimov et al. |
| 2015/0151134 A1 | 6/2015 | Efimov et al. |
| 2016/0243372 A1 | 8/2016 | Efimov et al. |

FOREIGN PATENT DOCUMENTS

| | | |
|---|---|---|
| EP | 2231263 A2 | 9/2010 |
| EP | 2566578 A2 | 3/2013 |
| GB | 2025236 A | 1/1980 |
| JP | 2005-515856 | 6/2005 |
| JP | 2006-504490 | 2/2006 |
| JP | 2006-507093 | 3/2006 |
| WO | WO 1996/011035 A1 | 4/1996 |
| WO | WO 2006/042295 A1 | 4/2006 |
| WO | WO 2006/052838 A2 | 5/2006 |
| WO | WO 2008/063498 A1 | 5/2008 |

OTHER PUBLICATIONS

Hou et al., Abstract of "Determination of ventricular vulnerable period and ventricular fibrillation threshold by use of T-wave shocks in patients undergoing implantation of cardioverter/defibrillators". Circulation, Nov. 1, 1995;92(9): 2258-64. 2 pgs.

Davidenko et al., "Stationary and drifting spiral waves of excitation in isolated cardia muscle," Nature, vol. 355, pp. 349-351, Jan. 23, 1992.

Gray et al., "Spatial and temporal organization during cardiac fibrillation," Nature, vol. 392, pp. 75-78, May 14, 1998.

Witkowski et al, "Spatiotemporal evolution of ventricular fibrillation," Nature, vol. 392, pp. 78-82, Mar. 5, 1998.

Cherry et al, "Visualization of spiral and scroll waves in simulated and experimental cardiac tissue", New J. Phys., vol. 10, pp. 125016-125059, 44 pages, 2008.

Koster et al., "A randomized trial comparing monophasic and biphasic waveform shocks for external cardioversion of atrial fibrillation," Am. Heart. J. vol. 147, pp. el-e7, 2004.

Babbs et al., "Therapeutic indices for transchest defibrillator shocks: Effective, damaging, and lethal electrical doeses," Am. Heart J., vol. 99, No. 6, pp. 734-738, Jun. 1980.

Santini et al., "Single Shock Endocavitary Low Energy Intracardiac Cardioversion of Chronic Atrial Fibrillation," J. Interv. Card. Electrophysiol., vol. 3, pp. 45-51, 1999.

Sakurai et al., "Design and Control of Wave Propagation Patterns in Excitable Media," Science, vol. 296, pp. 2009-2012, Jun. 14, 2002.

Rappel et al, "Spatiotemporal Control of Wave Instabilities in Cardiac Tissue," Phys. Rev. Lett., vol. 83, No. 2, pp. 456-459, Jul. 12, 1999.

Fenton et al., "Multiple mechanisms of spiral wave breakup in a model of cardiac electrical activity," Chaos, vol. 12, No. 3, pp. 852-892, Sep. 2002.

Fenton et al., "Vortex dynamics in three-dimensional continuous myocardium with fiber rotation: Filament instability and fibrillation," Chaos, vol. 8, No. 1, pp. 20-47, Mar. 1998.

Mackenzie, "Making sense of a heart gone wild," Science, vol. 303, pp. 786-787, Feb. 6, 2004.

Walcott et al., "Do clinically relevant transthoracic defibrillation energies cause myocardial damage and dysfunction?" Resuscitation, vol. 59, pp. 59-70, 2003.

Fenton et al., "Termination of Atrial Fibrillation Using Pulsed Low-Energy Far-Field Stimulation," Circulation, vol. 120, pp. 467-476, 2009.

Fast et al., "Activation of Cardiac Tissue by Extracellular Electrical Shocks: Formation of 'Secondary Sources' at Intercellular Clefts in Monolayers of Cultured Myocytes," Circ. Res., vol. 82, pp. 375-385, 1998.

Plonsey, "The Nature of Sources of Bioelectric and Biomagnetic Fields," Biophys. J., vol. 39, pp. 309-312, 1982.

Sambelashvili et al., "Virtual electrode theory explains pacing threshold increase caused by cardiac tissue damage," Am. J. Physiol. Heart Circ. Physiol., vol. 286, pp. H2183-H2194, 2004.

Hooks et al, "Cardiac Microstructure: Implications for Electrical Propagation and Defibrillation in the Heart," Circ. Res., vol. 91, pp. 331-338, 2002.

Trayanova et al., "Modeling Defibrillation: Effects of Fiber Curvature," J. Electrocardiol., vol. 31 (suppl.), pp. 23-29, 1998.

Roth et al., "A Bidomain Model for the Extracellular Potential and Magnetic Field of Cardiac Tissue," IEEE Trans. Biomed. Eng., vol. 33, No. 4, pp. 467-469, Apr. 1986.

Murray, "The Physiological Principle of Minimum Work: I. The Vascular System and the Cost of Blood Volume," Proc. Natl. Acad. Sci. USA, vol. 12, pp. 207-214, 1926.

Kassab, "Scaling laws of vascular trees: of form and function," Am. J. Physiol. Heart Circ. Physiol., vol. 290, pp. H894-H903, 2006.

Maleckar et al., "Polarity reversal lowers activation time during diastolic field stimulation of the rabbit ventricles: insights into mechanisms,"Am. J. Physiol. Heart Circ. Physiol., vol. 295, pp. H1626-H1633, 2008.

Kirchhof et al, "Regional entrainment of Atrial Fibrillation Studied by High-Resolution Mapping in Open-Chest Dogs," Circulation, vol. 88, pp. 736-749, 1993.

Pumir et al, "Wave Emission from Heterogeneities Opens a Way to Cotnrolling Chaos in the Heart," Phys. Rev. Lett., vol. 99, pp. 208101-1, 2007.

Gray et al, "Termination of spiral waves during cardiac fibrillation via shock-induced phase resetting," Proc. Natl. Acad. Sci. USA, vol. 102, No. 13, pp. 4672-4677, Mar. 29, 2005.

Gray et al., "Several small shocks beat one big one", vol. 475. Jul. 14, 2011. pp. 181-182.

Ladwig et al., "Absence of an Impact of Emotional Distress on the Perception of Intracardiac Shock Discharges," International Journal of Behavioral Medicine, 2003, 10(1):56-65, USA.

Fishler et al., "Spatiotemporal Effects of Syncytial Heterogeneities on Cardiac Far-field Excitations during Monophasic and Biphasic Shocks", Journal of Cardiovascular Electrophysiolgy, 1998, 9(12):1310-24, USA.

Efimov et al., "Virtual Electrode-Induced Phase Singularity: A Basic Mechanism of Defibrillation Failure," Circulation Research, 1998, 82(8):918-25, USA.

Efimov et al., "Transmembrane Voltage Changes Produced by Real and Virtual Electrodes During Monophasic Defibrillation Shock Delivered by an Implantable Electrode," Journal of Cardiovascular Electrophysiolgy, 1997, 8(9):1031-45, USA.

Cheng et al., "Virtual Electrode-Induced Reexcitation: A Mechanism of Defibrillation," Circulation Research, 1999, 85(22):1056-66, USA.

Fishier, "Syncytial Heterogeneity as a Mechanism Underlying Cardiac Far-Field Stimulation During Defibrillation-Level Shocks," Journal of Cardiovascular Electrophysiolgy, 1998, 9(4):384-94, USA.

Tsukerman et al., "Defibrillation of the Heart by a Rotating Current Field," Kariologiia, 1973, 13(12):75-80, USA.

Zheng et al., "Reduction of the Internal Atrial Defibrillation Threshold with Balanced Orthogonal Sequential Shocks," Journal of Cardiovascular Electophysiology, 2002; 13(9):904-9, USA.

Hucker et al,, "Atrioventricular conduction with and without AV nodal delay: two pathways to the bundle of His in the rabbit heart", Am J. Physiol. Heart Circ. Physiol., 2007, 293:H1122-H1130, USA.

Mowrey et al., "Membrane Time Constant During Internal Defibrillation Strength Shocks in Intact Heart: Effects of Na.sup.+ and Ca.sup.2+ Channel Blockers," J. Cardiovascular Electrophysiology, Apr. 25, 2004, Jun. 8, 2008, and Jan. 2009, 20(1):85-92, USA.

Sepulveda et al., "Current injection into a two-dimensional anisotropic bidomain", Biophys. J., vol. 55, May 1989, pp. 987-999, USA.

Allessie et al., "Regional Control of Atrial Fibrillation by Rapid Pacing in Conscious Dogs", Circulation, vol. 84, No. 4, Oct. 1991, pp. 1689-1697, USA.

(56) References Cited

OTHER PUBLICATIONS

Daoud et al., "Response of Type I Atrial Fibrillation to Atrial Pacing in Humans", Circulation, vol. 94, No. 5, 1996, 13 pages, USA.
Disertori et al., "Antitachycardia pacing therapies to terminate atrial tachyarrhythmias: the AT500 Italian Registry", European Heart Journal Supplements, 2001, pp. 16-24, USA.
Pumir et al., "Unpinning of a Rotating Wave in Cardiac Muscle by an Electric Field", J. Theor. Biol., vol. 199, 1999, pp. 311-319, USA.
N. S. Peters et al., "Disturbed Connexin43 Gap Junction Distribution Correlates With the Location of Reentrant Circuits in the Epicardial Border Zone of Healing Canine Infarcts That Cause Ventricular Tachycardia," Circulation, 1997, 95:988-996.
J. T. Niemann et al., "Intracardiac Voltage Gradients during Transthoracic Defibrillation: Implications for Postshock Myocardial Injury," Acad. Emerg. Med., Feb. 2005, 12(2):99-105.
I. Kodama et al., "Aftereffects of high-intensity DC stimulation of the electromechanical performance of ventricular muscle", Am. J. Physiol., 1994, 267:H248-H258.
H. G. Li et al., "Defribillation Shocks Produce Different Effects on Purkinje Fibers and Ventricular Muscle: Implications for Successful Defibrillation, Refibrillation and Postshock Arrhythmia", J Am Coll Cardiol, 1993, 22:607-614.
X. Zhou et al., "Epicardial Mapping of Ventricular Defibrillation With Monophasic and Biphasic Shocks in Dogs," Circulation Research, Jan. 1993, 72(2):145-160.
L. Li et al., "Mechanisms of enhanced shock-induced arrhythmogenesis in the rabbit heart with healed myocardial infaraction," Am. J. Physiol. Heart Circ Physiol., May 3, 2005, 289:H1054-H1068.
A. Sambelashvili et al., "Nonlinear effects in subthreshold virtual electrode polarization," Am. J. Physiol. Heart Circ, Physiol., 2003, 284(6):H2368-H2374.
F. Aguel et al., "Advances in Modeling Cardiac Defibrillation," Int'l Journal of Bifurcation & Chaos, 2003, 13(12):3791-3803.
M. Hillebrenner et al., "Postshock arrhythmogenesis in a slice of the canine heart," J. Cardiovasc. Electrophys., 2003, 14:S249-S256.
N. Trayanova et al., "Virtual Electrode-Induced Positive and Negative Graded Responses: New Insights into Fibrillation Induction and Defibrillation," J. Cardiovascular Electrophysicology, 2003, 14(7):756-763.
C. Larson et al., "Analysis of Electrically-Induced Reentrant Circuits in a Sheet of Myocardium," Annals Biomed. Eng., 2003, 31:768-780.
I. R. Efimov, "Filbrillatin or Neurillation: Back to the future in our concepts of sudden cardiac death?", Circ. Res., May 30, 2003, 92(10):1062-1064.
I. R. Efimov et al., "Diastolic Shocking Experience: Do Virtual Anodes Exist Only During Systole?", J. Cardiovascular Electrophysiology, Nov. 2003, 14(11):1223-1224.
I. R. Efimov et al., Fast Fluorescent Mapping of Electrical Activity in the Heart: Practical Guide to Experimental Design and Applications, Chapter 7, pp. 131-156.
Y. Cheng et al., "Shock-induced arrhythmogenesis is enhanced by 2,3-butanedione monoxime compared with cytochalasin D," Am. J. Physiol. Heart Circ. Physiol., 2004, 286:H310-H318.
S. Takagi et al., "Unpinning and Removal of a Rotating Wave in Cardiac Muscle", Phys. Review Letters, Jul. 30, 2004, 93(5):058101-1-058101-4.
L. Li et al., "Effects of Lidocaine on Shock-Induced Vulnerability", J. Cardiovascular Electrophysiology, Oct. 2003, 14(10):S237-S248.
Y. Cheng et al., "Mechanisms of Shock-Induced Arrhythmogenesis During Acute Global Ischemia", Am J Physiol. Heart Circ. Physiol., Jun. 2002, 282(6):H2141-51.
F. Qu et al., "Mechanisms of Superiority of Ascending Ramp Waveforms: New Insights into Mechanisms of Shock-induced Vulnerability and Defibrillation," Am. J. Physiol. Heart Circ. Physiol., 2005, 289:H569-H577.
T. Ashihara et al., "Spiral Wave Control by a Localized Stimulus: A Bidomain Model Study," J. Cardiovascular Electrophysiology, Feb. 2004 15(2):226-233.
C. Ramanathan, "Noninvasive electrocardiographic imaging for cardiac electrophysiology and arrhythmia," Nature Medicine, Apr. 2004, 10(4):422-428.
V. Nikolski et al., "Fluorescent Imaging of a Dual-Pathway Atrioventricular-Nodal Conduction System," Circ Res., Feb. 16, 2001, pp. 1-8.
F. Qu et al., "The Gurvich waveform has lower defibrillation threshold than the Zoll waveform and the truncated exponential waveform in the rabbit heart," Can. J. Physiol. Pharmacol., 2005, 83:152-160.
Grosu et al., "Learning and Detecting Emergent Behavior in Networks of Cardiac Myocytes", Communications of the ACM, Mar. 2009, pp. 97-104, vol. 52, No. 3.
Ripplinger et al., "Mechanisms of unpinning and termination of ventricular tachycardia", Am J. Physiol. Heart Circ. Physiol., 2006, pp. H184-H192.
Cartee et al., "The Transient Subthreshold Response of Spherical and Cylindrical Cell Models to Extracellular Stimulation", IEEE Trans. Biomed. Eng., vol. 39, No. 1, Jan. 1992, pp. 76-85.
Ideker et al., "Correlation Among Fibrillation, Defibrillation and Cardiac Pacing", Pacing Clin. Electrophysiol, vol. 18, Mar. 1995, pp. 512-525.
Sobie et al., "A Generalized Activating Function for Predicting Virtual Electrodes in Cardiac Tissue", Biophys. J., vol. 73, Sep. 1997, pp. 1410-1423.
Trayanova et al., "The Response of a Spherical Heart to a Uniform Electric Field: A Bidomain Analysis of Cardiac Stimulation", J. IEEE trans. Biomed. Eng., vol. 40, No. 9, Sep. 1993, pp. 899-908.
Chebbok et al., Low Energy Anti-Fibrillation Pacing (LEAP): A Gental, non traumatic defibrillation Option. European Heart Journal 33: 381-381 Suppl. 1, Aug. 2012.
Anderson, "The Anatomy of the Atrioventricular Node," Heart Rhythm Society, 7 pages, Apr. 16, 2012.
Supplementary Partial European Search Report for European Application No. 08858734.0, dated Nov. 17, 2011, 5 pages.
European Extended Search Report for European Application No. EP08858734.0 dated Nov. 17, 2011, 11 pages.
European Examination Report for European Application No. 08858734.0 dated Jul. 7, 2014, 4 pages.
Chinese Office Action for CN201180032063.X dated Apr. 2, 2014, 10 pages.
European Search Report for European Application No. 11777847.2 dated Nov. 5, 2013, 4 pages.
European Office Action for European Application No. 11777847.2 dated Jul. 18, 2014, 4 pages.
Japanese Notice of Reasons for Refusal for Japanese Application No. 2013-510116 dated Nov. 4, 2014, 2 pages (translation).
PCT Application No. PCT/US2008/086483, Written Opinion dated Jun. 25, 2009, 6 pages.
PCT Application No. PCT/US2008/086483, Search Report dated Jun. 25, 2009, 4 pages.
PCT Application No. PCT/US2011/033547, Search Report dated Jan. 17, 2012, 4 pages.
PCT Application No. PCT/US2011/033547, Written Opinion dated Jan. 17, 2012, 4 pages.
International Preliminary Report on Patentability for International Application No. PCT/US2011/033547 dated Nov. 22, 2012.
International Search Report for International Application No. PCT/US2007/023836 dated Apr. 9, 2008, 7 pages.
European Patent Office, European Office Action for European Application No. 05825356.8, dated Oct. 5, 2009, 6 pages, Munich, Germany.
Australian Patent Examination Report No. 1 for Australian Application No. 2008335087 dated Feb. 21, 2013.
European Search Report for European Application No. 11777847 dated Nov. 5, 2013, 4 pages.
Australian Patent Examination Report No. 1 for Australian Application No. 2011248794 dated Aug. 30, 2013.
Chinese Office Action from Chinese Application No. 200880126712.0 dated May 2, 2013.
Japanese Notice of Reasons for Rejection for Japanese Application No. 2010538168 dated Mar. 26, 2013. English translation provided.

(56) References Cited

OTHER PUBLICATIONS

Translation and Notice of Reason for Rejection dated Aug. 7, 2012 for Japanese Application No. 2010-538168.
Chinese Office Action from Chinese Application No. 200880126712.0 dated Nov. 27, 2012. Brief English Description.
Canadian Office Action and Examination Search Report from Canadian Application No. 2,709,287, dated Apr. 23, 2015, 5 pages.
Application and File History for U.S. Appl. No. 12/776,196, filed May 7, 2010, now U.S. Pat. No. 8,560,066. Inventor: Efimov et al.
Application and File History for U.S. Appl. No. 12/518,343, filed Sep. 2, 2009, now U.S. Pat. No. 8,391,995. Inventors: Efimov et al.
Application and File History for U.S. Appl. No. 12/333,257, filed Dec. 11, 2008, now U.S. Pat. No. 8,509,889. Inventors: Efimov et al.
Application and File History for U.S. Appl. No. 11/266,755, filed Nov. 3, 2005, now U.S. Pat. No. 8,175,702. Inventors: Efimov et al.
Application and File History for U.S. Appl. No. 13/464,537, filed May 4, 2012, now U.S. Pat. No. 8,639,325. Inventors: Efimov et al.
Application and File History for U.S. Appl. No. 13/349,527, filed Jan. 12, 2012, now U.S. Pat. No. 8,874,208. Inventors: Efimov et al.
Application and File History for U.S. Appl. No. 13/349,517, filed Jan. 12, 2012, now U.S. Pat. No. 8,706,216. Inventors: Efimov et al.
Application and File History for U.S. Appl. No. 14/524,712, filed Oct. 27, 2014, Inventors: Efimov et al.
Application and File History for U.S. Appl. No. 14/165,230, filed Jan. 27, 2014, Inventors Efimov et al., now U.S. Pat. No. 9,067,079.
Application and File History for U.S. Appl. No. 14/753,773, filed Jun. 29, 2015, Inventors Efimov et al.
Ripplinger, Crystal May. "The Role of Myocardial Heterogeneity in Maintenance and Termination of Cardiac Arrhythmias", Dissertation, Graduate School of Arts and Sciences, Washington University, Department of Biomedical Engineering, May 2008, 166 pgs.
Application and File History for U.S. Appl. No. 14/257,620, filed Apr. 21, 2014, Inventors Efimov et al., now U.S. Pat. No. 9,289,620.
English translation of Office Action from Japanese Application JP 2015-133157, dated May 23, 2016, 6 pgs.
Office Action from Canadian Application CA 2,709,287, dated Apr. 27, 2016, 3 pgs.
Application and File History for U.S. Appl. No. 15/054,885, filed Feb. 26, 2016, inventors Efimov et al.

\* cited by examiner

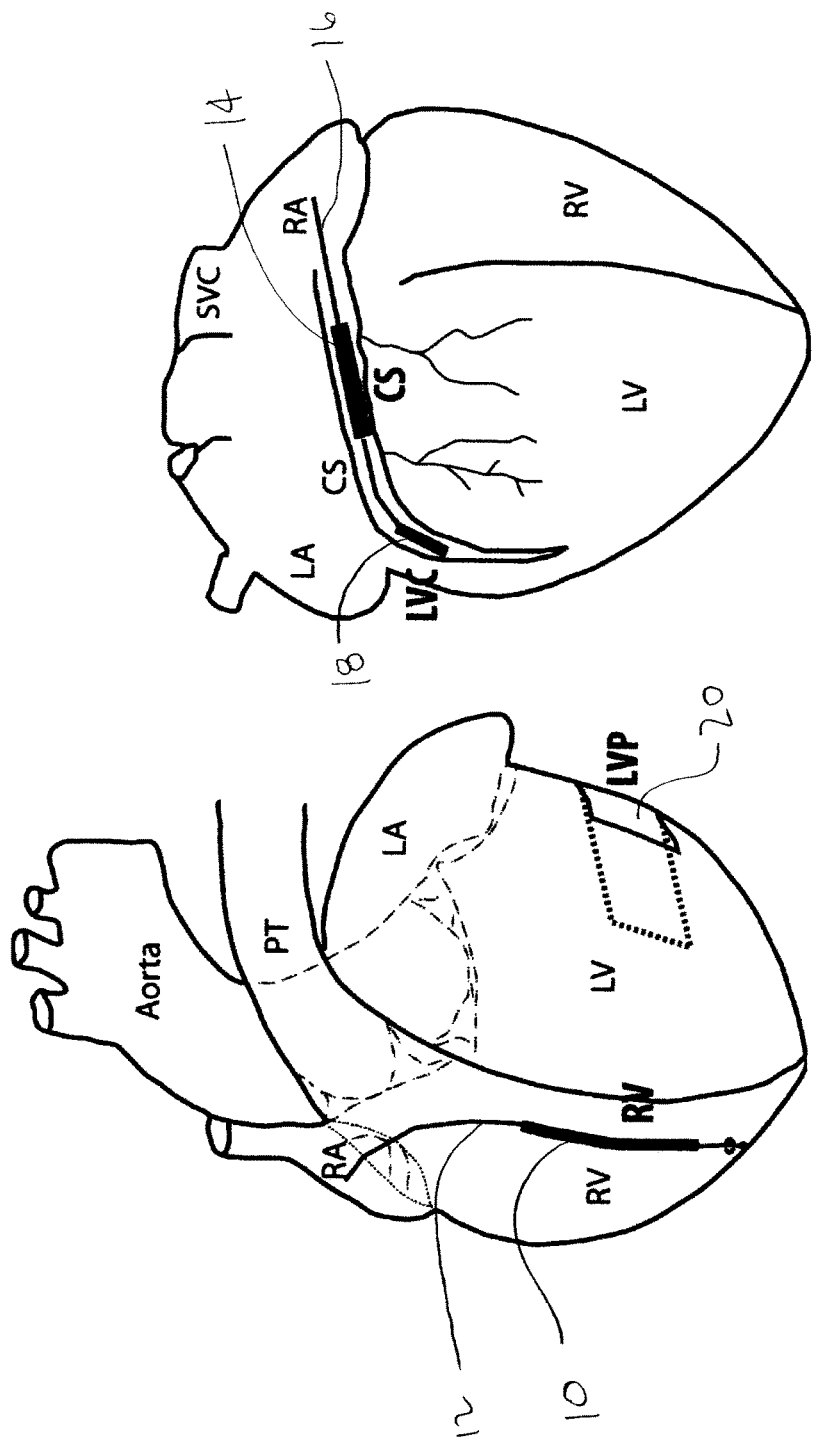

METHODS AND DEVICES FOR MULTI-STAGE VENTRICULAR THERAPY

RELATED APPLICATIONS

The present application is a continuation of U.S. patent application Ser. No. 14/524,712, filed Oct. 27, 2014, now U.S. Pat. No. 9,526,907, which is a continuation of U.S. patent application Ser. No. 13/349,527, filed Jan. 12, 2012, now U.S. Pat. No. 8,874,208, which is a continuation-in-part of U.S. patent application Ser. No. 12/776,196, filed May 7, 2010, now U.S. Pat. No. 8,560,066, which is a continuation-in-part of U.S. patent application Ser. No. 12/333,257, filed Dec. 11, 2008, now U.S. Pat. No. 8,509,889, which claims the benefit of U.S. Provisional Application No. 61/012,861, filed Dec. 11, 2007, each of which is incorporated herein by reference.

FIELD OF THE INVENTION

The present disclosure relates generally to the treatment of ventricular arrhythmias. More particularly, the present disclosure relates to devices and methods of using low-energy electrical stimuli from an implantable device that delivers a three-stage ventricular cardioversion and defibrillation therapy to destabilize and extinguish reentry mechanisms that maintain ventricular tachycardia and ventricular fibrillation.

BACKGROUND OF THE INVENTION

It is well-known that rotating waves of electrical activity are a factor in potentially dangerous cardiac arrhythmias such as ventricular tachycardia and ventricular fibrillations (VT/VF). The rotating waves, or reentries, that are responsible for ventricular tachycardia events are classified into two categories: 1) functional reentries, which involve freely rotating waves; and 2) anatomical reentries, where a wave rotates around an obstacle such as a blood vessel or piece of ischemic tissue. The latter are referred to as being 'pinned' by the obstacle. Traditional defibrillation is not a preferred way of dealing with such rotating waves because defibrillation resets electrical activity everywhere in the heart and uses high voltage shocks, which have undesirable side effects.

One common method of attempting to terminate these rotating waves or reentries is anti-tachycardia pacing (ATP). ATP has a high rate of success in dealing with functional reentries, but is not as effective against anatomical reentries. Generally, if ATP is not effective, a defibrillation shock of large amplitude is applied directly to cardiac muscle.

Such high voltage, high energy shocks may be delivered by a standard external defibrillator with the patient sedated during delivery of a defibrillation shock. However, in order to provide an external shock that can effectively terminate arrhythmias with electrodes placed externally on the body, such systems must provide higher energy shocks than would be required by implantable devices. In addition, externally applied shocks necessarily recruit more of the skeletal musculature resulting in potentially more pain and discomfort to the patient.

Another method of treatment for patients experiencing ventricular tachycardia (VT) or ventricular fibrillation (VF) is the implantable cardioverter defibrillator ("ICD"). However, the energy level needed for successful cardioversion can also exceed the pain threshold. Endocardial cardioversion shock energies greater than 0.1 J are perceived to be uncomfortable (Ladwig, K. H., Marten-Mittag, B., Lehmann, G., Gundel, H., Simon, H., Alt, E., Absence of an Impact of Emotional Distress on the Perception of Intracardiac Shock Discharges, International Journal of Behavioral Medicine, 2003, 10(1): 56-65), and patients can fail to distinguish energy levels higher than this and find them equally painful. The pain threshold depends on many factors, including autonomic tone, presence of drugs, location of electrodes and shock waveforms. Moreover, pain thresholds can be different from patient to patient. Further, as compared to external defibrillators, ICD's present other challenges, including a limited energy source.

Many systems have sought to lower the energy level required for effective atrial fibrillation. A number of systems, such as, for example, U.S. Pat. No. 5,282,836 to Kreyenhagen et al., U.S. Pat. No. 5,797,967 to KenKnight, U.S. Pat. Nos. 6,081,746, 6,085,116 and 6,292,691 to Pendekanti et al., and U.S. Pat. Nos. 6,556,862 and 6,587,720 to Hsu et al. disclose application of atrial pacing pulses in order to lower the energy level necessary for atrial defibrillation shocks. The energy delivered by pacing pulses is relatively nominal in comparison to defibrillation shocks. U.S. Pat. No. 5,620,468 to Mongeon et al. discloses applying cycles of low energy pulse bursts to the atrium to terminate atrial arrhythmias. U.S. Pat. No. 5,840,079 to Warman et al. discloses applying low-rate ventricular pacing before delivering atrial defibrillation pulses. U.S. Pat. No. 5,813,999 to Ayers et al. discloses the use of biphasic shocks for atrial defibrillation. U.S. Pat. Nos. 6,233,483 and 6,763,266 to Kroll discloses the use of multi-step defibrillation waveform, while U.S. Pat. No. 6,327,500 to Cooper et al. discloses delivering two reduced-energy, sequential defibrillation pulses instead of one larger energy defibrillation pulse.

However, reduced-energy AF treatments do not necessarily translate well to VT or VF treatments in part due to the physiological differences in the causes of AF vs. VF, but also in part due to the criticality of VT and VF.

Consequently, there remains a need for improved VT and VF treatment methods and devices enabling successful electrical treatment without exceeding the pain threshold of a patient.

SUMMARY OF THE INVENTION

Embodiments of methods and apparatus in accordance with the present disclosure provide for a three-stage ventricular cardioversion and defibrillation therapy to treat ventricular tachycardias (VTs) and ventricular fibrillation (VF) within pain tolerance thresholds of a patient. A VT/VF therapy in accordance with various embodiments includes an implantable therapy generator adapted to generate and selectively deliver a three-stage ventricular therapy and at least two leads operably connected to the implantable therapy generator, each lead having at least one electrode adapted to be positioned proximate the ventricle of a heart of the patient. The ventricular arrhythmia treatment device is programmed with a set of therapy parameters for delivering a three-stage cardioversion or defibrillation therapy to a patient via both a far-field configuration and a near-field configuration of the electrodes upon detection of a ventricular arrhythmia by the ventricular arrhythmia treatment device.

In an embodiment, the three-stage therapy comprises a three-stage ventricular therapy that includes a first stage for unpinning of one or more singularities associated with a ventricular arrhythmia, a second stage for anti-repinning of the one or more singularities associated with the ventricular arrhythmia, and a third stage for extinguishing of the one or more singularities associated with the ventricular arrhythmia. In various embodiments, the first stage has two to ten biphasic far field ventricular cardioversion/defibrillation pulses of two volts to 100 volts delivered within one to two VT/VF cycle lengths (CLs). The second stage comprises six to ten far field pulses of one to five times the ventricular shock excitation threshold, generally 0.5 to 20 volts, with a pulse coupling interval of between 70-100% of VT/VF cycle length. The third stage comprises eight to twelve near field pulses at a voltage of two to four times the strength of the diastolic ventricular pacing threshold, with a pulse coupling interval of between 70-100% of the VT/VF cycle length. The three-stage ventricular therapy is delivered in response to detection of the ventricular arrhythmia, with each stage having an inter-stage delay of 50 to 800 milliseconds, and in some embodiments, without confirmation of conversion of the ventricular arrhythmia until after delivery of the third stage.

In various embodiments, a ventricular arrhythmia treatment apparatus includes at least one electrode adapted to be implanted proximate a ventricle of a heart of a patient to deliver far field pulses and at least one electrode adapted to implanted proximate a ventricle of the heart of the patient to deliver near field pulses and sense cardiac signals. An implantable therapy generator is operably connected to the electrodes and includes a battery system operably coupled and providing power to sensing circuitry, detection circuitry, control circuitry and therapy circuitry of the implantable therapy generator. The sensing circuitry senses cardiac signals representative of ventricular activity. The detection circuitry evaluates the cardiac signals representative of ventricular activity to determine a ventricular cycle length and detect a ventricular arrhythmia. The control circuitry, in response to the ventricular arrhythmia, controls generation and selective delivery of a three-stage ventricular therapy to the electrodes with each stage having an inter-stage delay of between 50 to 800 milliseconds. The therapy circuitry is operably connected to the electrodes and the control circuitry and includes at least one first stage charge storage circuit selectively coupled to the at least one far field electrode that selectively stores energy for a first stage of the three-stage ventricular therapy, at least one second stage charge storage circuit selectively coupled to the at least one far field electrode that selectively stores a second stage of the three-stage ventricular therapy, and at least one third stage charge storage circuit selectively coupled to the near field electrode that selectively stores a third stage of the three-stage ventricular cardioversion therapy.

The methods and devices of the present disclosure can exploit a virtual electrode polarization ("VEP") enabling successful treatment of VT or VF with an implantable system without exceeding the pain threshold of a patient. This is enabled by far-field excitation of multiple areas of tissue at once, rather than just one small area near a pacing electrode, which can be more effective for both VT and VF. The methods can differ from conventional defibrillation therapy, which typically uses only one high-energy (about five to about forty-one joules) monophasic or biphasic shock or two sequential monophasic shocks from two different vectors of far-field electrical stimuli.

The methods and devices of embodiments of the present disclosure can utilize a low-voltage phased unpinning far-field therapy together with near-field therapy that forms the three-stage ventricular cardioversion therapy to destabilize or terminate the core of a mother rotor, which anchors to a myocardial heterogeneities such as scar from myocardial infarction, coronary arteries or other fibrotic areas. A significant reduction in the energy required to convert a ventricular arrhythmia can be obtained with this unpinning, anti-repinning and then extinguishing technique compared with conventional high-energy defibrillation, thus enabling successful cardioversion without exceeding the pain threshold of a patient.

Applying far-field low energy electric field stimulation in an appropriate range of time- and frequency-domains can interrupt and terminate the reentrant circuit by selectively exciting the excitable gap near the core of reentry. By stimulating the excitable gap near the core of the circuit, the reentry can be disrupted and terminated. The reentrant circuit is anchored at a functionally or anatomically heterogeneous region, which constitutes the core of reentry. Areas near the heterogeneous regions (including the region of the core of reentry) will experience greater polarization in response to an applied electric field compared with the surrounding, more homogeneous tissue. Thus, the region near the core of reentry can be preferentially excited with very small electric fields to destabilize or terminate anchored reentrant circuits. Once destabilized, subsequent shocks can more easily terminate the arrhythmia and restore normal sinus rhythm.

Virtual electrode excitation can be used at local resistive heterogeneities to depolarize a critical part of the reentry pathway or excitable gap near the core of reentry. Various pulse protocols for a three-stage ventricular cardioversion/defibrillation therapy to terminate ventricular arrhythmias in accordance with aspects of the present invention are contemplated. In one aspect, the reentry is either terminated directly or destabilized by far-field pulses delivered in a first and second stage and then terminated by additional stimuli by near-field pulses delivered in a third stage of the three-stage therapy. The low energy stimulation can be below the pain threshold and, thus, may cause no anxiety and uncomfortable side effects to the patient. In another aspect, a phased unpinning far-field therapy can be delivered in response to a detected ventricular arrhythmia, with post treatment pacing administered as a follow-up therapy to the phased unpinning far-field therapy.

To further optimize this low energy method of termination, multiple electric field configurations can be used to optimally excite the excitable gap near the core of reentry and disrupt the reentrant circuit. These field configurations can be achieved by placing several defibrillation leads/electrodes into the right ventricle, coronary sinus, and the left ventricular veins. Electric fields can be delivered between any two or more of these electrodes as well as between one of these electrodes and the device itself (hot can configuration). In another aspect, segmented electrodes with the ability to selectively energize one or more of the electrode segments can be used. Modulation of the electric field vector can then be used to achieve maximum coverage of the heart.

In another aspect of the present invention, the morphology of an electrogram of an arrhythmia can be documented, stored, and compared to previously stored morphologies. Anatomic location(s) of the reentry circuit(s) may be determined by the specific anatomy and physiological remodeling of the atria, which are unique for each patient. The embodiment takes advantage of the observation that several morphologies of ventricular arrhythmias tend to occur with higher frequency than others. Optimization of electric field configuration and pulse sequence of the therapy may be conducted separately for each electrogram morphology and stored in memory for future arrhythmia terminations. When an arrhythmia is detected, it will be determined whether the morphology of the electrogram of an arrhythmia is known. If it is, the optimized therapy stored in memory may be applied to convert that arrhythmia.

In another aspect of the present invention, an implantable cardiac therapy device for treating a in need of defibrillation includes one or more sensors comprising one or more implanted electrodes positioned in different locations for generating electrogram signals, one or more pacing implanted electrodes positioned in different locations for near-field pacing of different sites, one or more implanted defibrillation electrodes positioned in different locations for far-field delivery of electrical current, and an implantable or external device which can be capable to deliver a train of pulses.

In one exemplary embodiment, the implantable device is implanted just under the left clavicle. This location places the device in approximate alignment with the longitudinal anatomical axis of the heart (an axis through the center of the heart that intersects the apex and the inter-ventricular septum). When the electrodes are implanted in this manner, the arrangement of the device and electrodes is similar in configuration to the top of an umbrella: the device constituting the ferrule of an umbrella, and the electrodes constituting the tines of the umbrella. The electrodes of the device are energized in sequential order to achieve electrical fields of stimulation that is similar to "stimulating" the triangles of umbrella fabric, one after the other, in either a clockwise or counter-clockwise manner or in a custom sequence. Leads may be active or passive fixation.

BRIEF DESCRIPTION OF THE DRAWINGS

The invention may be more completely understood in consideration of the following detailed description of various embodiments of the invention in connection with the accompanying drawings, in which:

FIG. 1A depicts a schematic anterior view of a human heart and anatomical locations of implantable defibrillation leads, with a lead placed in the right ventricle (RV), and an epicardial patch (LVP) placed over the left ventricle;

FIG. 1B depicts a schematic posterior view of a human heart and anatomical locations of implantable defibrillation leads with a lead placed in the coronary sinus (CS) and the left ventricular vein (LVC);

Figure 2A:
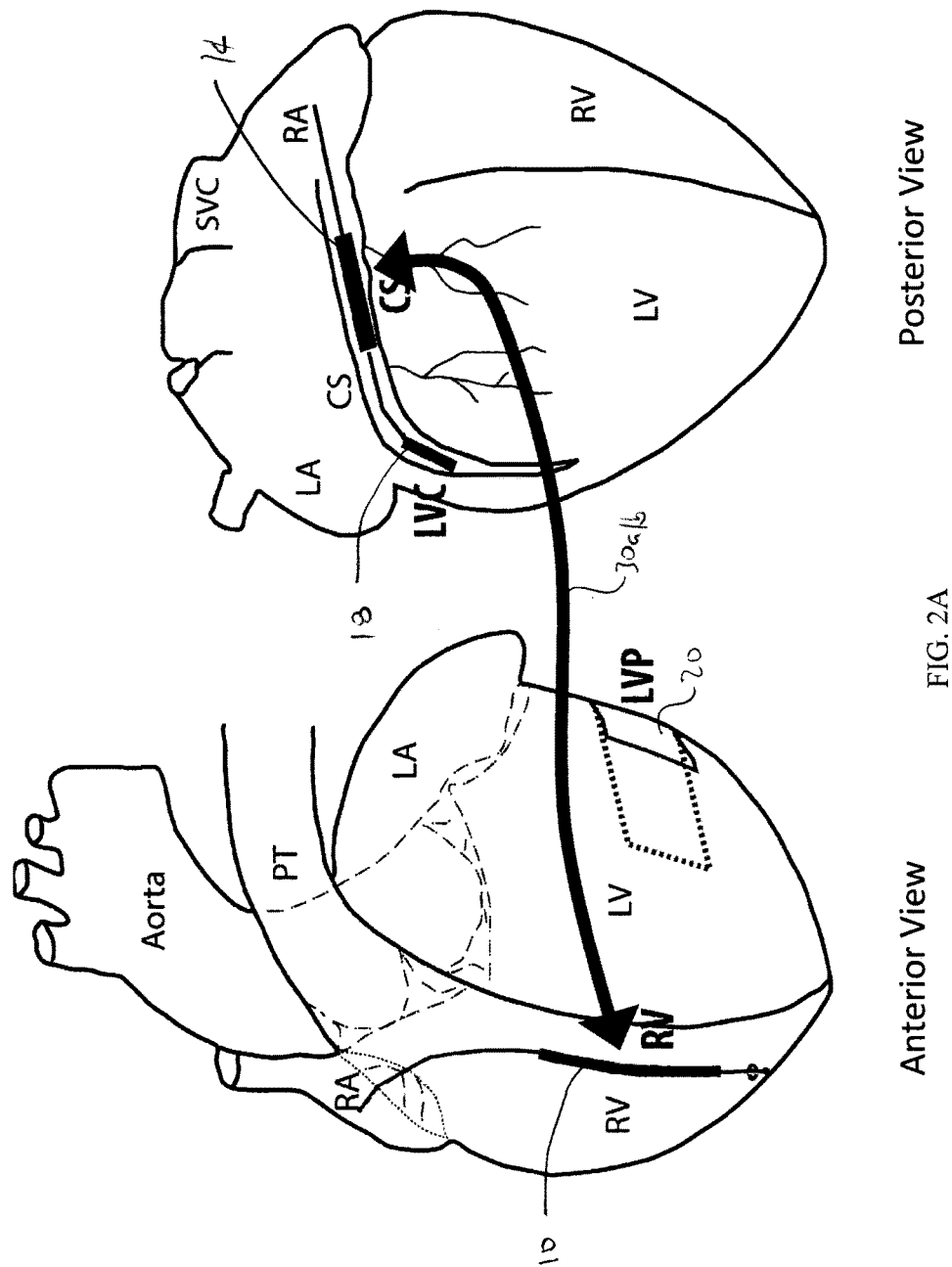
FIGS. 2A-E depict multiple simplified schematic anterior and posterior views of a human heart, depicting various anatomical locations of implantable defibrillation leads and electrodes, with arrows indicating electric field vectors between leads and electrodes.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

Embodiments of the present disclosure are based on a low-voltage phased unpinning far-field therapy together with near-field therapy that forms the three-stage ventricular cardioversion and defibrillation therapy for destabilizing and subsequently terminating anatomical reentrant tachyarrhythmias. A significant reduction in the energy required to convert a ventricular arrhythmia can be obtained with this unpinning, anti-repinning and then extinguishing technique compared with conventional high-energy defibrillation. Furthermore, the low-energy, ventricular therapy enables successful cardioversion without exceeding the pain threshold of a patient. With respect to pain and pain-related subject matter described hereinafter, it will be understood that such description generally relates to cardioversion of ventricular tachycardia (VT), rather than conversion of ventricular fibrillation (VF). Further, it will be understood the term "cardioversion" refers specifically to cardioversion of a VT, and that defibrillation refers specifically to defibrillation of a VF, though in some instances, cardioversion may in a broad sense be used to describe termination of a ventricular arrhythmia that may comprise VT or VF.

The anatomical structure of cardiac tissue can be inherently heterogeneous. These syncytial heterogeneities of even modest proportions can represent a significant mechanism contributing to the far-field excitation process. Fishler, M. G., Vepa K., Spatiotemporal Effects of Syncytial Heterogeneities on Cardiac Far-field Excitations during Monophasic and Biphasic Shocks, Journal of Cardiovascular Electrophysiology, 1998, 9(12): 1310-24, which is incorporated herein by reference.

For purposes of the present application, the term "near-field," can relate to effects that are in close proximity to stimulating electrode(s), i.e., distances are restricted by several space constants (lambda) of cardiac tissue, which is typically up to several millimeters. Near-field effects can be strongly dependent upon distance from the electrodes. The term "far-field," on the other hand, can relate to effects that are generally independent or less dependent upon distance from the electrodes. They can occur at distances that are much greater than the space constant (lambda).

Applying far-field low energy electric field stimulation in a range of time- and frequency-domains can interrupt and terminate the reentrant circuit by selectively exciting the excitable gap near the core of reentry. High frequency far-field electric stimulation has significantly higher defibrillation success compared to near-field ATP. The reentrant circuit can be anchored at a functionally or anatomically heterogeneous region, which constitutes the core of reentry. The virtual electrode theory of myocardial excitation by electric field predicts that areas near the core will experience greater polarization in response to an applied electric field compared with the surrounding, more homogeneous tissue. Various shock protocols to terminate ventricular arrhythmias are contemplated. Thus, in one aspect, the region near the core of reentry can be preferentially excited with very small electric fields to destabilize or terminate anchored reentrant circuits. Once destabilized, subsequent shocks can more easily drive the rotors away to the boundary of atrial tissue and restore normal sinus rhythm.

In traditional high-voltage defibrillation therapy, a truncated exponential biphasic waveform has a lower defibrillation energy as compared to monophasic shocks. However, in the case of phased unpinning far-field therapy ("PUFFT"), the use of multiple monophasic versus multiple biphasic waveforms was recently found to be more effective in terminating ventricular tachycardias in a rabbit model. This difference was thought to exist because optimal biphasic defibrillation waveforms may not produce VEPs because of an asymmetric effect of phase reversal on membrane polarization. Efimov, I. R., Cheng, Y., Van Wagoner, D. R., Mazgalev, T., Tchou, P. J., Virtual Electrode-Induced Phase Singularity: A Basic Mechanism of Defibrillation Failure, Circulation Research, 1998, 82(8): 918-25, which is incorporated herein by reference. VEP is discussed further in Efimov, I. R., Cheng, Y. N., Biermann, M., Van Wagoner, D. R., Mazgalev, T. N., Tchou, P. J., Transmembrane Voltage Changes Produced by Real and Virtual Electrodes During Monophasic Defibrillation Shock Delivered by an Implantable Electrode, Journal of Cardiovascular Electrophysiology, 1997, 8(9): 1031-45; Cheng, Y. N., Mowrey, K. A., Van Wagoner, D. R., Tchou, P. J., Efimov, I. R., Virtual Electrode-Induced Reexcitation: A Mechanism of Defibrillation, Circulation Research, 1999, 85(11):1056-66; and Fishler, M. G., Syncytial Heterogeneity as a Mechanism Underlying Cardiac Far-Field Stimulation During Defibrillation-Level Shocks. Journal of Cardiovascular Electrophysiology, 1998, 9(4): 384-94, all of which are incorporated herein by reference.

The ventricular defibrillation threshold ("DFT") can be significantly decreased by an orthogonally rotating current field. Tsukerman, B. M., Bogdanov, Klu, Kon, M. V., Kriukov, V. A., Vandiaev, G. K., Defibrillation of the Heart by a Rotating Current Field, Kardiologiia, 1973, 13(12): 75-80, which is incorporated herein by reference.

Virtual electrode excitation can be used at local resistive heterogeneities to depolarize a critical part of the reentry pathway or excitable gap near the core of reentry. Thus, reentry can be terminated directly or destabilized and then the reentry can be terminated by additional stimuli. This technique can be exploited in an implantable or external device, which, upon sensing a ventricular tachyarrhythmia, can apply the low energy stimulation. Also, the low energy stimulation can be expected to be below the pain threshold and thus may cause no anxiety and uncomfortable side effects to the patient.

To further optimize the low energy method of termination, multiple electric field configurations can be used to optimally excite the excitable gap near the core of reentry and disrupt the reentrant circuit. Referring to FIGS. 1A and 1B, schematic anterior and posterior views of a human heart and anatomical locations of implantable defibrillation leads and sensing electrodes are depicted. As will be described further below, shock pulses from a therapy first stage and a second stage are applied between transvenous, implantable endocardial defibrillation electrodes, including electrode 10 of lead 12 placed in the right ventricle (RV), electrode 14 of lead 16 placed in the coronary sinus (CS), and electrode 18 of lead 16 placed in the left ventricular veins draining into the coronary sinus (LVC). As an alternative to LVC, a defibrillation patch 20 could be placed over the LV epicardium (LVP). One or multiple vectors will be used for energy delivery from electrodes in the RV, CS, and left ventricle (either LVC or LVP). Pacing stimuli applied in a therapy third stage may be applied from the tip to coil or tip to ring of any of the RV, CS or LV leads.

Referring to FIGS. 2A to 2E, using three electrodes and the implantable device itself, the electric shock field can be continuously or incrementally rotated to effectively have a large number of combinations for selecting the shock vector. This includes reversing the shock polarity between two electrodes. For example, each individual shock pulse may be directed through a different vector. The sequence of switching the vectors among shocks may also be changed, to create a large number of possible electric fields between the RV, CS, and LVC (or LVP) defibrillation coils. In an embodiment, an optimization of the three-stage therapy of the present invention will take place during a learning phase by a neural network of the device based on specific VT electrogram morphologies in each patient.

Electric fields can be delivered between any two of these electrodes as well as between one of these electrodes and the device itself. Modulation of the electric field vector can be used to achieve maximum coverage of the heart and to maintain an optimal Virtual Electrode Polarization pattern through the entire cycle of arrhythmia in order to depolarize the maximum area of excitable gaps. The optimal electric fields used and the correct sequence of fields can also be explored on a trial and error basis for each patient or can be estimated based on external information regarding potential sites of the reentrant circuits, or can be based on a combination of both.

Figure 2B:
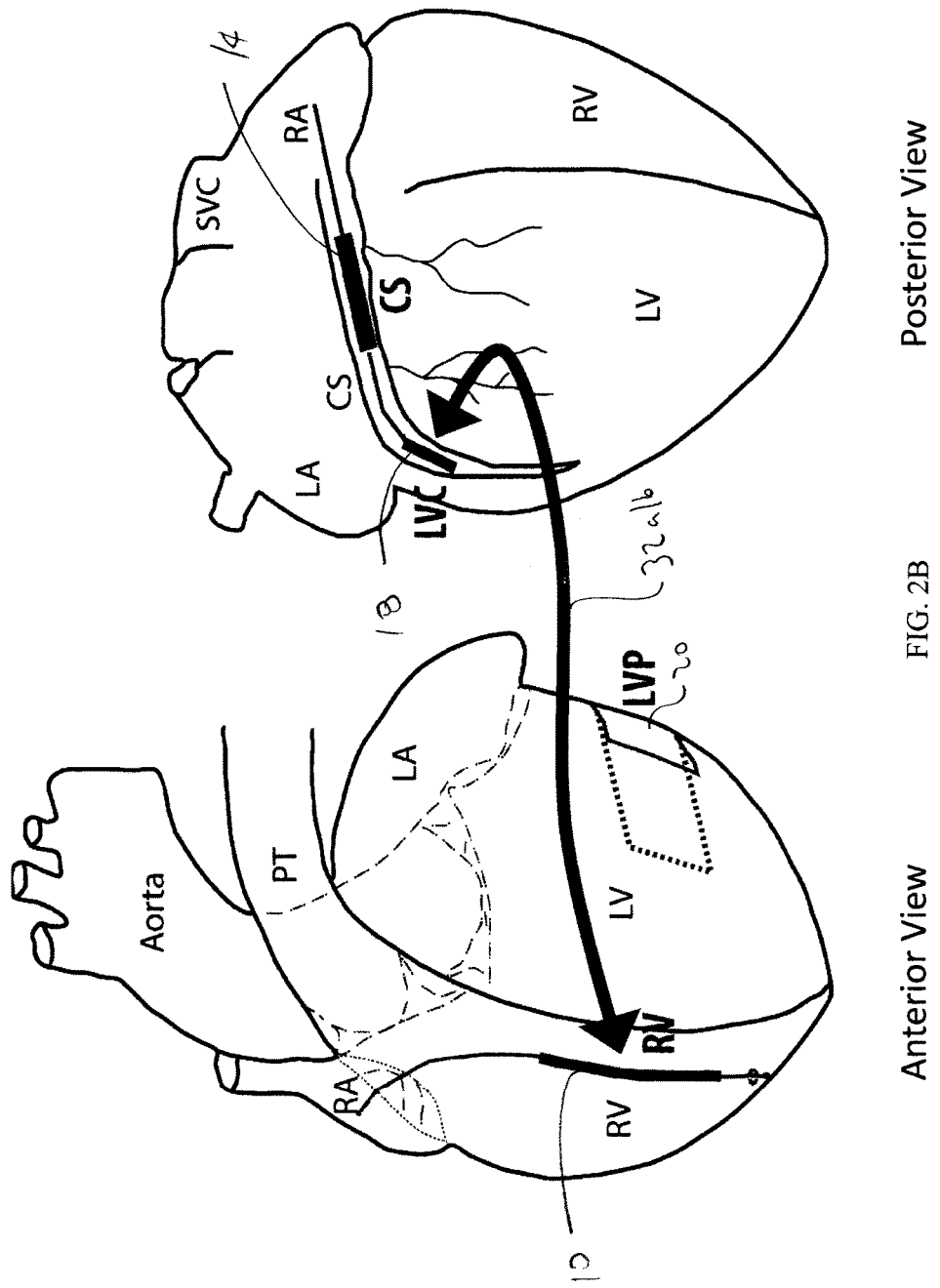
Figure 2C:
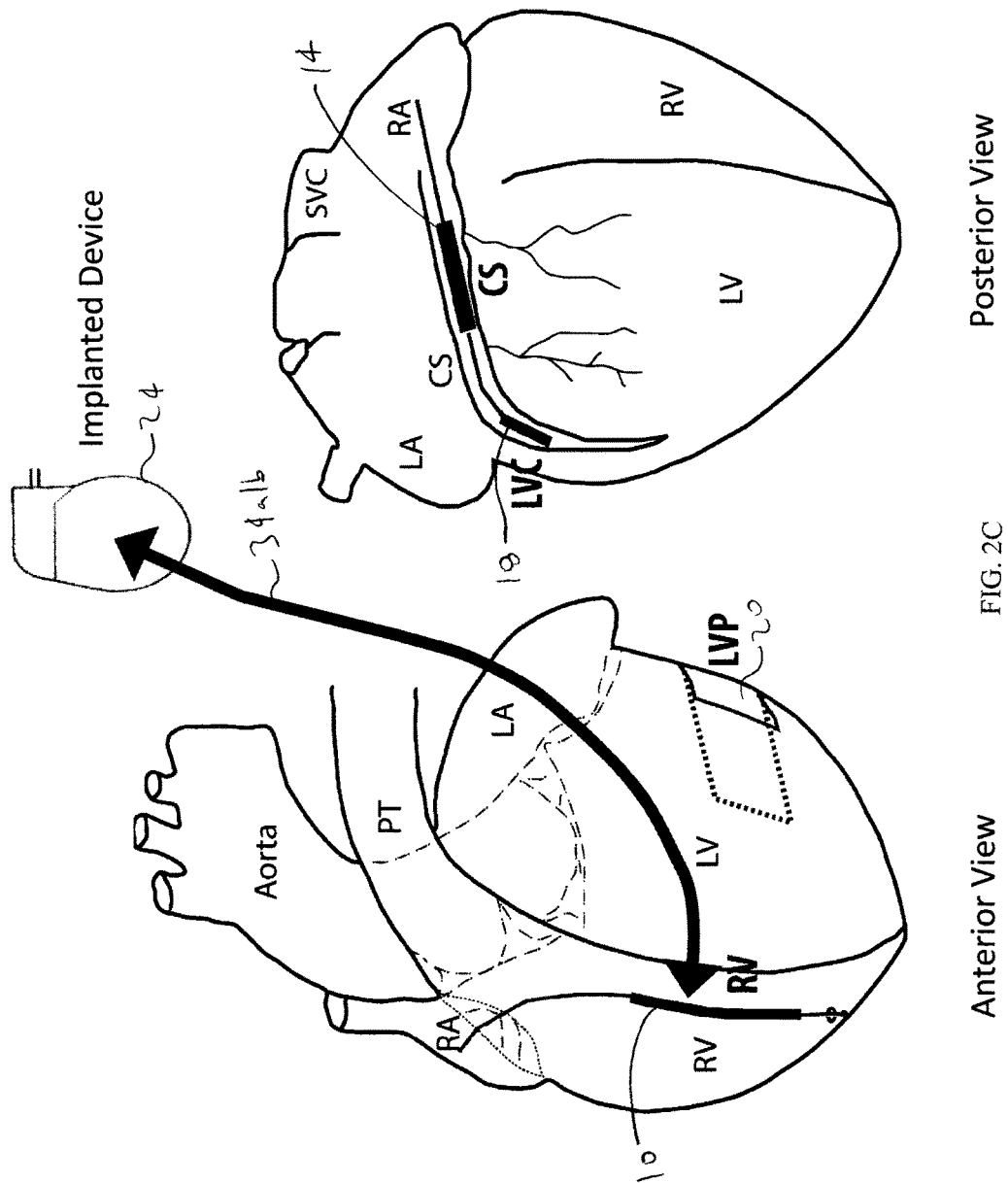
Figure 2D:
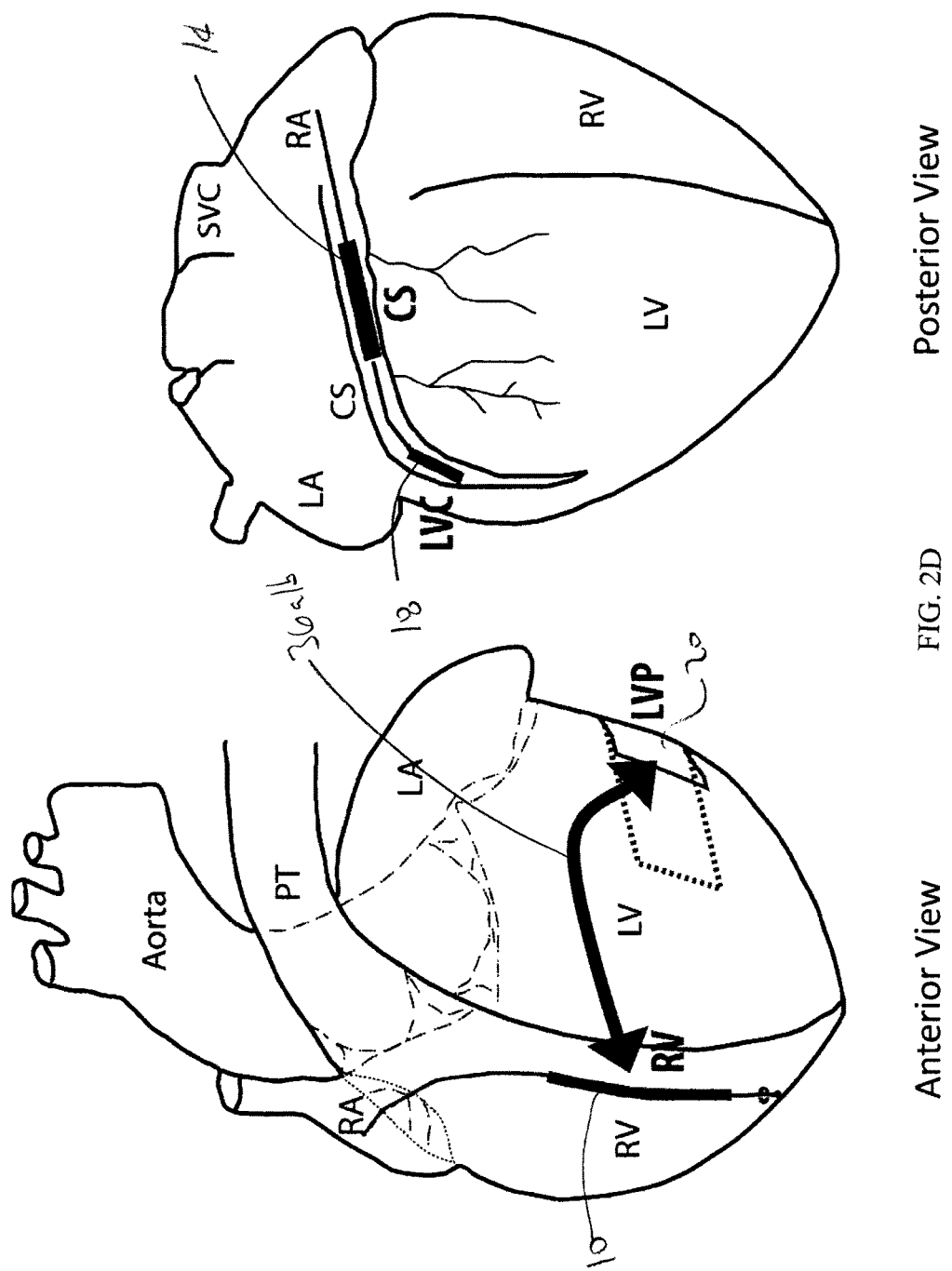
Figure 2E:
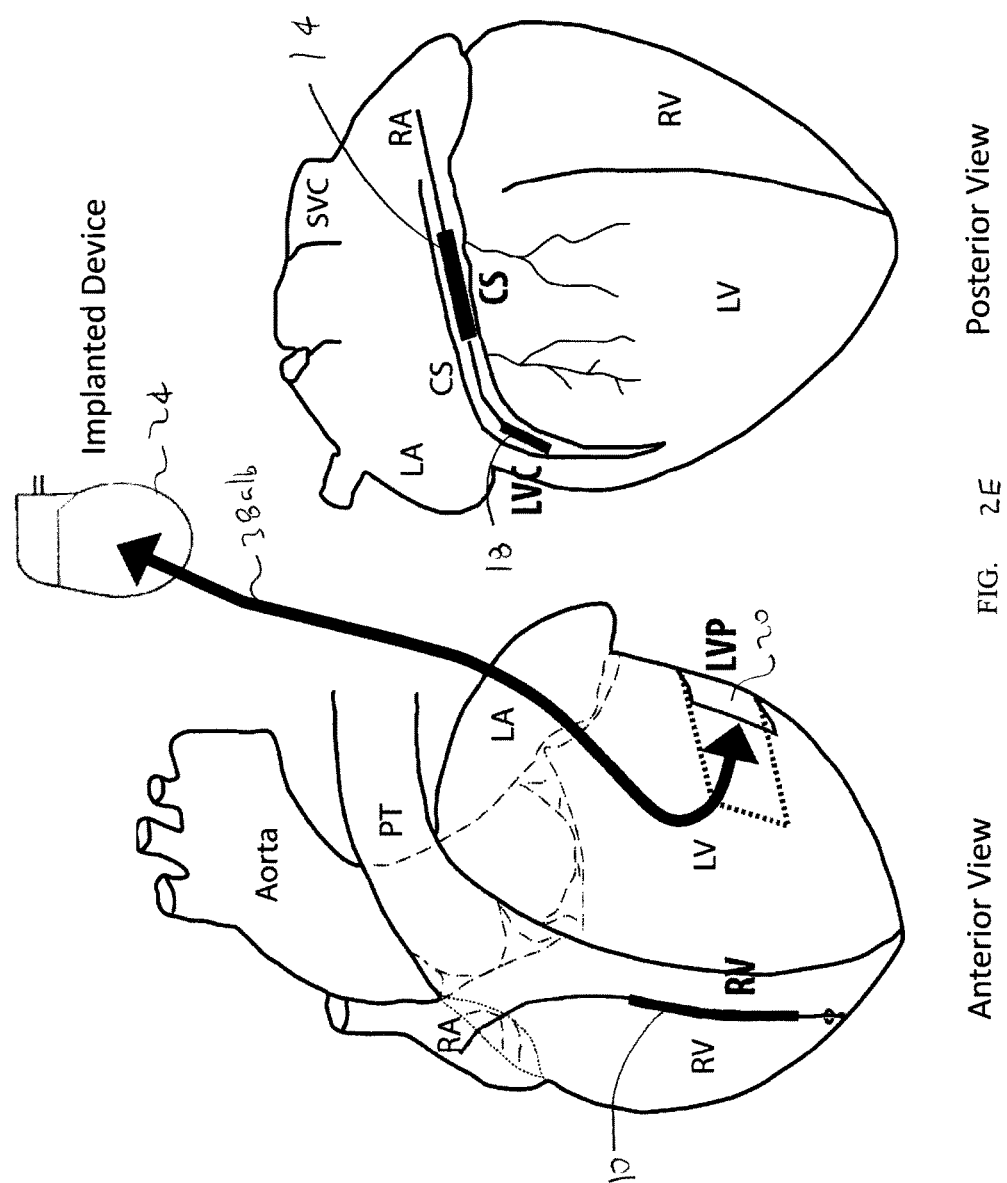

FIG. 2A depicts a pair of electric field shock vectors 30a/b between an electrode 10 in the RV and an electrode 14 in the CS (vector 30a being from the RV to the CS, and vector 30b being from the CS to the RV); FIG. 2B depicts a pair of electric field vectors 32a/b between an electrode 10 in the RV and an electrode 18 in the LVC (vector 32a being from the RV to the LVC, and vector 32b being from the LVC to the RV); FIG. 2C depicts a pair of electric field vectors 34a/b between an electrode 10 in the RV and to the "active/hot can" comprising an implantable device 24 (vector 34a being from the RV to the device 24, and vector 34b being from the device 24 to the RV); FIG. 2D depicts a pair of electric field vectors 36a/b between an electrode 10 in the RV and an electrode patch 20 at the LVP (vector 36a being from the RV to the LVP, and vector 36b being from the LVP to the RV); and FIG. 2E depicts a pair of electric field vectors 38a/b between an electrode patch 20 at the LVP to implantable device 24 (vector 38a being from the LVP to device 24, and vector 38b being from the device 24 to the LVP).

Multiple, monophasic shock pulses can be applied with intervals as a function of arrhythmia cycle length. In one example, the far field unpinning shocks can be square waves, 10 ms in duration of which the voltage and vectors will be varied to determine minimum termination voltage. In other embodiments, the far field unpinning shocks or pulses may be rounded, staggered, ascending, descending, biphasic, multiphasic or variations thereof.

While a number of lead and electrode placements are described above, generally speaking, an optimal electrode configuration is one that maximizes current density across the heart, particularly in the region where the arrhythmia arises, thereby maximizing depolarization in the region originating the arrhythmia.

An algorithm may be used for treatment of VT or VF. The device can first estimate the mean CL of the arrhythmia. In addition, an algorithm can be used to characterize and categorize morphologies of a ventricular electrogram in order to use this information for patient-specific and morphology-specific optimization of phased unpinning far-field therapy.

An optimum time to apply the phased unpinning far-field therapy relative to the cardiac cycle may be determined from ventricular sensing electrodes including RV or far-field R-wave detection. Examples of finding unsafe times for far-field shock are also described in U.S. Pat. No. 5,814,081.

Other timing considerations, particularly with respect to phase or stage durations, may be determined in whole or in part by characteristics of the sensed ventricular tachyarrhythmia (VT or VF). As will be described below, ventricular activity, such as R-wave characteristics, may be used to determine an overall therapy timing, such as a maximum window of time for therapy delivery.

Learning algorithms may also used to optimize therapy on subsequent terminations. Once the optimal timing and field settings are achieved for a patient to terminate a ventricular tachyarrhythmia, these settings may be the starting point for termination of the next occurrence of VF.

In some embodiments, therapy can be optimized using a trial and error approach combined with learning algorithms to tailor therapy for each patient. The optimization includes two objectives: (a) terminating tachycardia and (b) avoiding intensities associated with pain.

As described above, the pain threshold depends on many factors, including autonomic tone, presence of drugs, location of electrodes and shock waveforms. A value of 0.1 J has been reported by Ladwig, K. H., Marten-Mittag, B., Lehmann, G., Gundel, H., Simon, H., Alt, E., Absence of an Impact of Emotional Distress on the Perception of Intracardiac Shock Discharges, International Journal of Behavioral Medicine, 2003, 10(1): 56-65, which is incorporated herein by reference, as the energy value where pain and/or discomfort is first generally experienced. However, it can be different from patient to patient. Thus, a real-time feedback to the patient can be provided in estimating the pain threshold during either the implantation or calibration of the device or during execution of the optimizing learning algorithms.

In one embodiment, the morphology of an arrhythmia's electrogram can be documented, stored, and compared to previously stored morphologies. Anatomic location(s) of the reentry circuit(s) are determined by the specific anatomy and physiological remodeling of the ventricle, which are unique for each patient. Thus, the morphologies can reveal the specific anatomic locations of the reentry circuits. Optimization of the pulse sequence of the therapy can be conducted separately for each electrogram morphology and stored in memory for future arrhythmia terminations.

Because this device, in certain embodiments, can deliver a series of electric field stimuli in rapid succession, traditional implantable pulse generators, such as those normally used in ICDs generally may be inadequate for the device. Traditional implantable pulse generators employ a charging period (on the order of seconds) to charge a capacitor, then rapidly discharge the capacitor to apply the shock. Before the next shock application, the capacitor may need to be charged again. In this device, several low energy far field unpinning shocks/pulses (two-ten) can be applied in rapid succession, which in some embodiments is determined by the VT or VF cycle length (CL) for each unpinning shock.

The implantable pulse generator according to one type of embodiment of this device can include several smaller capacitors that charge before or during the defibrillation trials. For each stimulus delivered, a single capacitor discharges with the appropriate amount of energy followed sequentially by a discharge from another capacitor until the appropriate number of stimuli is delivered. The capacitors can all be charged simultaneously before the entire defibrillation trial or, alternatively, the capacitors can be charged sequentially in groups, or individually. In one example implementation, capacitors which are used for unpinning shocks are charged while other unpinning shocks are applied. In a related example, a capacitor that is used for an earlier unpinning shock is re-charged during a subsequent one or more shock, and is further re-used for a later unpinning shock. This latter example is facilitated in embodiments where the power supply is capable of sufficient current drive to charge the capacitors in sufficient time to permit their re-use within the same trial.

In a related embodiment, the device uses multiple capacitors for storing the electrotherapy energy, except that, unlike the example embodiment described above, each capacitor has sufficient energy storage to provide more than a single shock in the sequence.

In order to produce the appropriate stimuli across the appropriate lead configuration, a fast-switching network can be employed to switch the discharged energy between the different capacitors as well as switching the applied energy to the correct electrodes. The pretreatment of pulses is described further in U.S. Pat. Nos. 5,366,485 and 5,314,448, both of which are incorporated herein by reference.

It is contemplated that the method of the present invention can be utilized together with, or separate from, other pacing and defibrillation therapies. For example, the present invention can be implemented as part of an ICD where a high voltage defibrillation shock can be delivered in the event that the method of the present invention is unable to successfully convert a cardiac arrhythmia. Alternatively, the present invention could be implemented as part of a conventional pacemaker to provide for an emergency response to a VT/VF condition in the patient that would increase the chances of patient survival.

The methods of the present invention also contemplate the use of any number of arrangements and configurations of waveforms and waveshapes for the electrical stimulation pulse(s). Known monophasic, biphasic, triphasic and cross-phase stimulation pulses may be utilized. In one embodiment, the present invention contemplates the use of an ascending ramp waveform as described in the article Qu, F., Li, L., Nikolski, V. P., Sharma, V., Efimov, I. R., Mechanisms of Superiority of Ascending Ramp Waveforms: New Insights into Mechanisms of Shock-induced Vulnerability and Defibrillation, American Journal of Physiology—Heart and Circulatory Physiology, 2005, 289: H569-H577, the disclosure of which is incorporated herein by reference.

The methods of the present invention also contemplate the use of any number of arrangement and configurations for the generation of the phased unpinning far field electrical stimulation pulse(s). While conventional high voltage capacitor discharge circuitry may be utilized to generate the lower energy stimulation pulse(s) in accordance with the present invention, it is also expected that alternative arrangements could be utilized involving lower voltage capacitor arrangements, such as stacked, switched or secondary capacitors, rechargeable batteries, charge pump and voltage booster circuits as described, for example, in U.S. Pat. Nos. 5,199,429, 5,334,219, 5,365,391, 5,372,605, 5,383,907, 5,391,186, 5,405,363, 5,407,444, 5,413,591, 5,620,464 and 5,674,248, the disclosures of each of which are incorporated herein by reference. Generation of the staged/phased unpinning far field therapy in accordance with embodiments of the present invention can be accomplished by any number of methods, including known methods for generating pacing pulses. Similarly, any number of known techniques for cardiac arrhythmia detection may be used in accordance with the method of the present invention.

Figure 3:
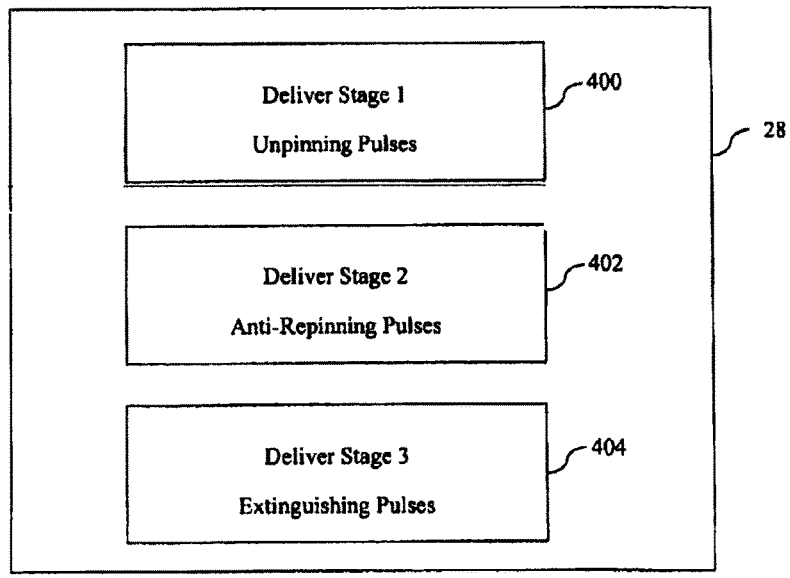
FIG. 3 depicts an embodiment of a three-stage ventricular therapy, according to an embodiment of the claimed invention.

In accordance with one embodiment the PUFFT three-stage therapy is delivered as part of a three-stage ventricular therapy. As shown in FIG. 3, in one embodiment the three-stage therapy of the present invention comprises a three-stage ventricular cardioversion and defibrillation therapy delivered to the patient in response to detection of a ventricular arrhythmia, the three-stage ventricular therapy having a set of therapy parameters and having a first stage (400) and a second stage (402) delivered via a far field configuration of the electrodes and a third stage (404) delivered via a near field configuration of the electrodes.

It will be understood that "three stage" ventricular therapy refers to all variations of therapies of the claimed invention that include at least one set of first-stage pulses, at least one set of second-stage pulses, and at least one set of third-stage pulses. It will also be understood that "multi-therapy" includes multiple three-stage therapies, wherein the ventricular arrhythmia may be reevaluated between three-stage therapy implementations.

Figure 4:
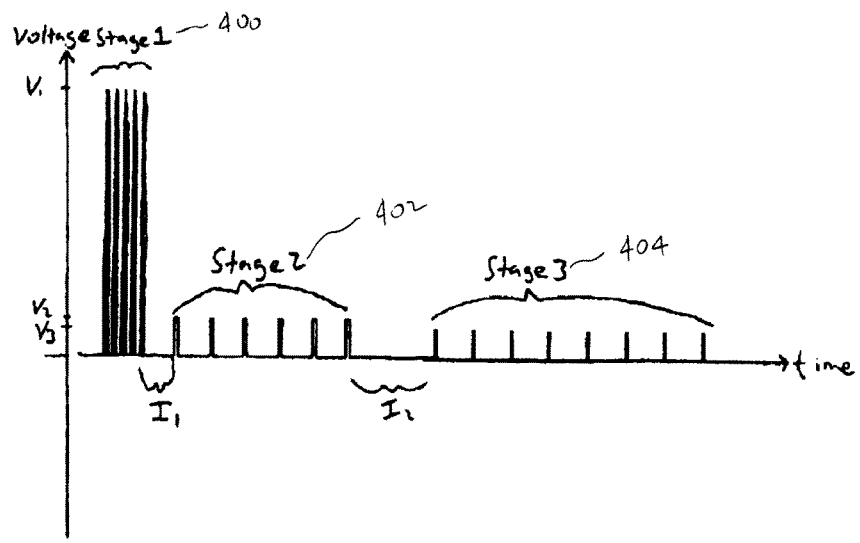
FIG. 4 depicts an embodiment of a stimulation waveform of the three-stage therapy of FIG. 3.

Referring to FIG. 4, a combined representation of three of the stages of the three-stage ventricular therapy is shown. A first stage (400) is applied for unpinning of one or more singularities associated with a ventricular arrhythmia. A second stage (402) is applied for anti-repinning of the one or more singularities associated with the ventricular arrhythmia. A third stage (404) is applied for extinguishing of the one or more singularities associated with the ventricular arrhythmia.

In various embodiments, the first stage (400) has at least two and up to ten ventricular cardioversion/defibrillation pulses of 2 volts to 100 volts. In other embodiments, particularly for VF pulse voltage may be as high as 200 volts, and in other embodiments as high as 400 volts, but still with an overall therapy energy significantly lower than traditional therapies. While depicted as monophasic, first stage (400) pulses may alternatively comprise biphasic or other multiphasic pulses. Pulse duration may be approximately 3-4 milliseconds in some embodiments, or, more generally, equal to or less than 10 milliseconds in various other embodiments. In an embodiment, first stage (400) pulses are delivered within one or two VT/VF cycle lengths.

In some embodiments, the arrhythmia will be reassessed after applying first stage (400) pulses. In other embodiments, the arrhythmia will not be reassessed until all stages of the therapy have been delivered.

In an embodiment, an interstage delay (I1) of 50 to 800 milliseconds precedes the second stage (402), though in other embodiments, interstage delay I1 may be shorter or longer.

In some embodiments, the second stage (402) comprises six to ten ultra-low energy monophasic or multiphasic far field pulses. In an embodiment, the minimum voltage amplitude of second stage (402) pulses is set to the ventricular shock excitation threshold (vSET), defined as the minimum voltage at which a far field pulse captures (excites) the ventricle. Typical shock pulse voltage for this stage is 0.5 to 20V. Though depicted as monophasic pulses, second stage (402) may comprise multiphasic or another non-traditional configuration. In an embodiment, second-stage pulse duration ranges from 5 ms to 20 milliseconds with a pulse coupling interval ranging from 70% to 100% of the cycle length of the ventricular tachycardia or ventricular fibrillation cycle length (VT/VF CL).

In some embodiments, the tachyarrhythmia will be reassessed after applying first stage (400) and second stage (402) pulses. In other embodiments, the tachyarrhythmia will not be reassessed until all stages of the therapy have been delivered.

An interstage delay (I2) of between 50 to 800 milliseconds precedes the third stage (404), though in other embodiments, interstage delay I2 may be shorter or longer.

In some embodiments, the third stage (404) comprises eight to twelve near-field pacing stimuli, a near-field entrainment, which facilitates the previous two stages to drive the tachyarrhythmia to termination. Though depicted as monophasic pulses, third stage (404) may comprise multiphasic or another non-traditional configuration. In an embodiment, third stage (404) pulses are applied through an endocardial defibrillation/pacing electrode at 2-4 times the strength of the diastolic pacing threshold, with a pulse duration of more than 0.2 and less than 5 milliseconds, and a pulse coupling interval of 70 to 100% of the VT/VF CL.

Figure 5:
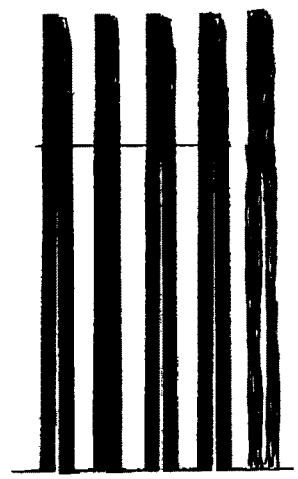
FIG. 5 depicts an embodiment of a first, unpinning stage of the waveform of FIG. 4.

Referring to FIG. 5, an embodiment of first stage (400) is shown. In this embodiment, each of five monophasic pulses is delivered from a separate output capacitor arrangement where an H-bridge output switching arrangement reversals the polarity of the far-field electrodes at some point during the discharge of the output capacitor arrangement. In alternate embodiments, fewer output capacitor arrangements may be used where later cardioversion pulses are delivered from the same output capacitor arrangement that was used to delivery an earlier cardioversion pulse and that has been recharged before the later cardioversion pulse. In other embodiments, each phase of the biphasic cardioversion pulse may be delivered from a separate output capacitor arrangement. In other embodiments, a switching capacitor network may be used to combine output capacitor arrangements to deliver the cardioversion pulses of the first stage (400). It will be understood that the initial output voltage, reversal voltage (in the case of an alternative biphasic pulse), duration and coupling interval between pulses may be the same or different for all or for some of the pulses within the range of pulse parameters provided for the first stage (400). It will also be understood that the pulses shown in FIG. 5 of the first stage (400) may all be delivered through the same far-field electrode configuration, and in other embodiments the pulses may be delivered as part of a rotating set of PUFFT pulses delivered through different far-field electrode configurations.

Figure 6:
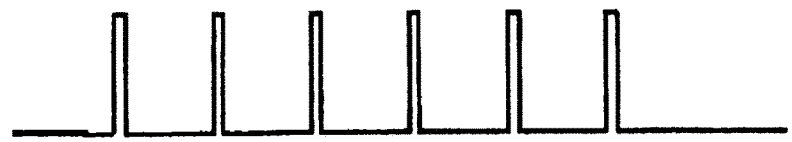
FIG. 6 depicts an embodiment of a second, anti-repinning stage of the waveform of FIG. 4.

Referring to FIG. 6, an embodiment of the second stage (402) is shown. In this embodiment, each of six monophasic far-field low voltage pulses are delivered from the same output capacitor arrangement that is recharged between successive pulses, although the pulses may each be delivered from separate output capacitor arrangements or from fewer output capacitor arrangements than the total number of pulses in the second stage (402). Alternatively, the pulses may be delivered directly from a charge pump, voltage booster or other similar kind of charge storage and/or delivery arrangement powered by a battery system. As with the first stage (400), it will be understood that the initial output voltage, duration and coupling interval between pulses of the second stage (402) may be the same or different for all or for some of the pulses within the range of pulse parameters provided for the second stage (402). It will also be understood that the pulses shown in FIG. 6 of the second stage (402) may all be delivered through the same far-field electrode configuration, and in other embodiments the pulses may be delivered as part of a rotating set of PUFFT pulses delivered through different far-field electrode configurations. The far-field electrode configuration for the second stage (402) may be the same as, or different than, the far-field electrode configuration utilized for the first stage (400).

Figure 7:
FIG. 7 depicts an embodiment of a third, extinguishing stage of the waveform of FIG. 4.

Referring to FIG. 7, an embodiment of the third stage (404) is shown. In this embodiment, each of eight monophasic near-field low voltage pulses are delivered from the same output capacitor arrangement that is recharged between successive pulses, although the pulses may each be delivered from separate output capacitor arrangements or from fewer output capacitor arrangements than the total number of pulses in the third stage (404). Alternatively, the pulses may be delivered directly from a charge pump, voltage booster or other similar kind of charge storage arrangement powered by a battery system. In one embodiment, the same output capacitor arrangement is used to deliver the second stage pulses and the third stage pulses. As with the first stage (400) and second stage (402), it will be understood that the initial output voltage, duration and coupling interval between pulses of the third stage (404) may be the same or different for all or for some of the pulses within the range of pulse parameters provided for the third stage (404). It will also be understood that the pulses shown in FIG. 14 of the third stage (404) may all be delivered through the same near-field electrode configuration, and in other embodiments the pulses may be delivered as part of a rotating set of PUFFT pulses delivered through different near-field electrode configurations. In some embodiments, the near-field electrode configuration may be a monopolar electrode arrangement, and in other embodiments, the near-field electrode configuration may be a bipolar electrode arrangement.

Figure 8:
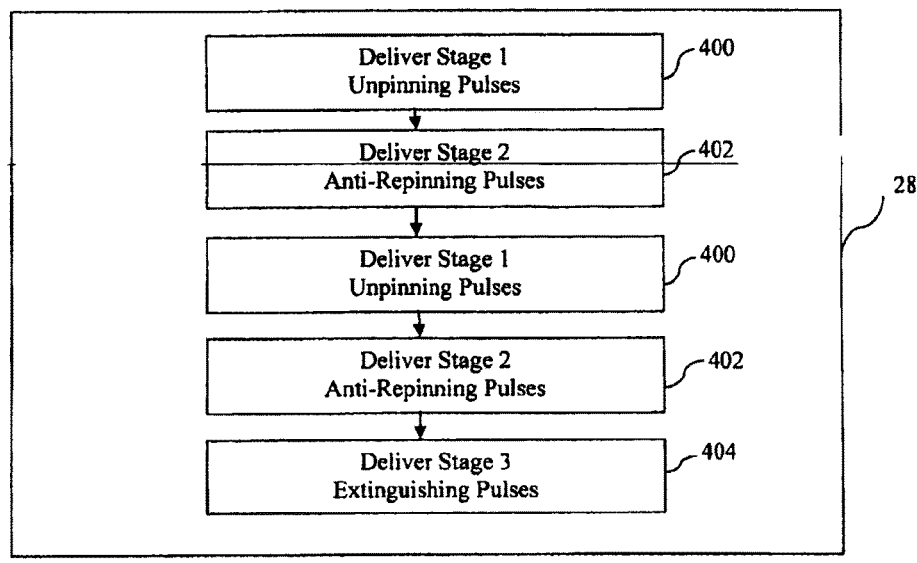
FIG. 8 depicts another embodiment of applying stimulation in the form of a three-stage ventricular therapy.
Figure 9:
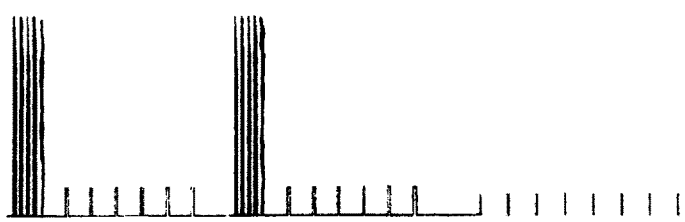
FIG. 9 depicts an embodiment of a stimulation waveform of the three-stage ventricular therapy of FIG. 8.

Referring to FIGS. 8 and 9, an alternate embodiment of the three-stage ventricular cardioversion/defibrillation therapy is shown. In this embodiment, the unpinning first stage (400) and anti-repinning second stage (402) are each repeated in sequence as part of the overall ventricular therapy (28) before delivery of the extinguishing third stage (404). As with the embodiment shown in FIG. 4, the parameters for each of the stages, and each of the pulses within each stage, may be the same or different for different stages and/or different pulses within each stage.

Figure 10:
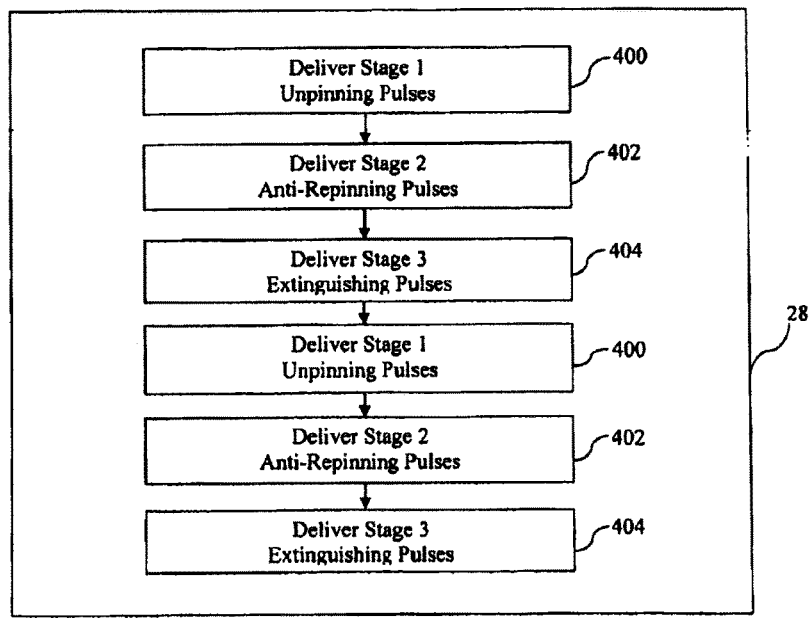
FIG. 10 depicts yet another embodiment of applying stimulation in the form of a three-stage ventricular therapy.
Figure 11:
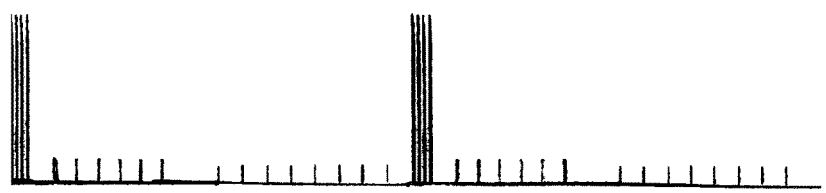
FIG. 11 depicts yet another embodiment of a stimulation waveform of the three-stage therapy of FIG. 10.

Referring to FIGS. 10 and 11, an alternate embodiment of the three-stage ventricular cardioversion/defibrillation therapy is shown. In this multi-therapy embodiment, the unpinning stage 1 (400) and anti-repinning stage 2 (402), as well as the extinguishing stage 3 (404) are each repeated in sequence as part of the overall ventricular cardioversion/defibrillation therapy (28), followed by a repeated delivery of all three of the stages before completion of the ventricular cardioversion/defibrillation therapy (28). As with the embodiment shown in FIG. 4, the parameters for each of the stages, and each of the pulses within each stage, may be the same or different for different stages and/or different pulses within each stage.

As described above, the three-stage ventricular therapy of the present invention may use various combination of each of the individual first, second, and three stages, depending on the different types of arrhythmias and morphology of ventricular electrograms. For example, the first stage and the second stage can be repeated several times, and then followed by the third stage, as depicted and described with respect to FIGS. 8 and 9. Consequently, combinations include, but are not limited to (referring to stages): 1-2-3; 1-2-1-2-3; 1-1-2-2-3-3, and so on.

Figure 12A:
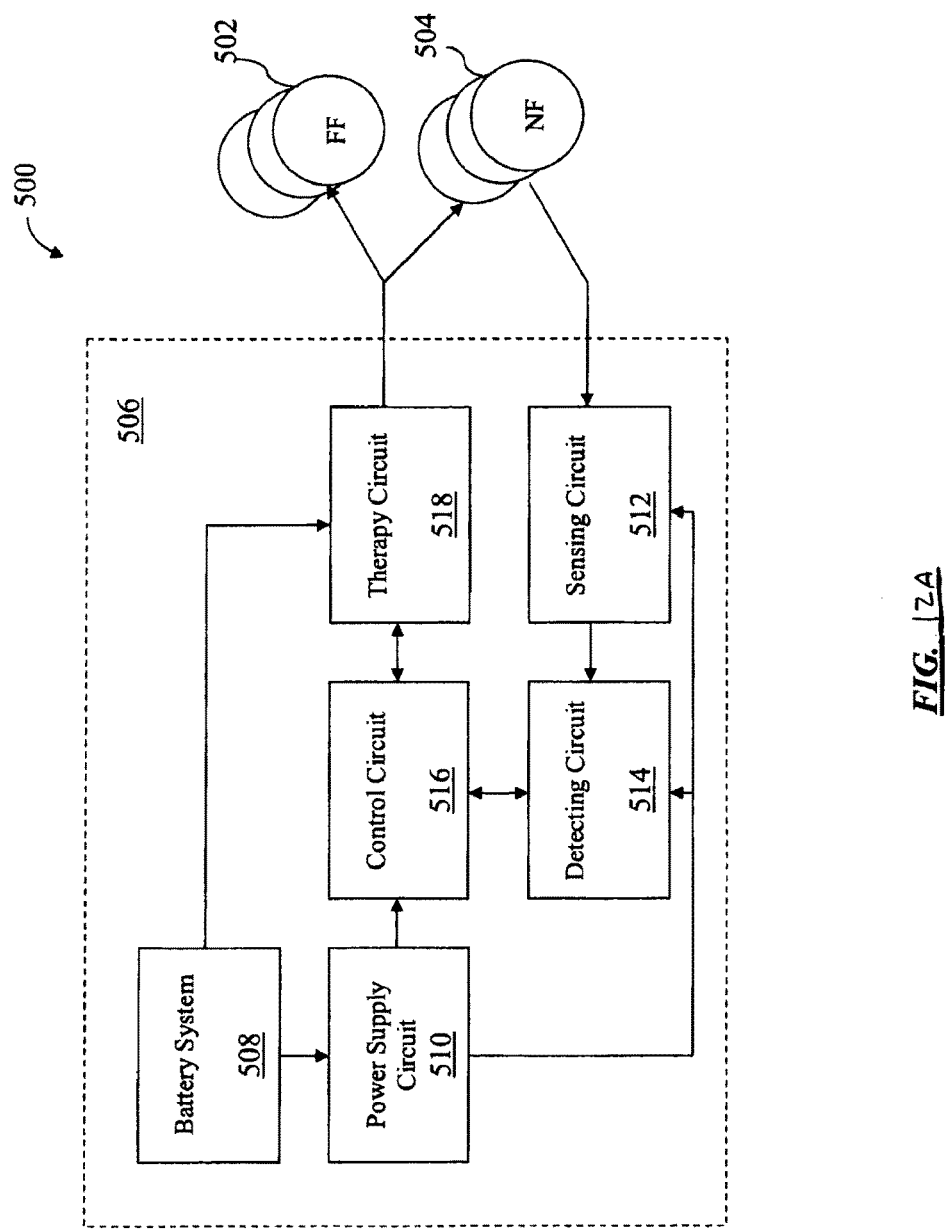
FIGS. 12A and 12B are block diagrams depicting of an embodiment of a three-stage ventricular therapy device, and the therapy circuitry thereof, respectively.
Figure 12B:
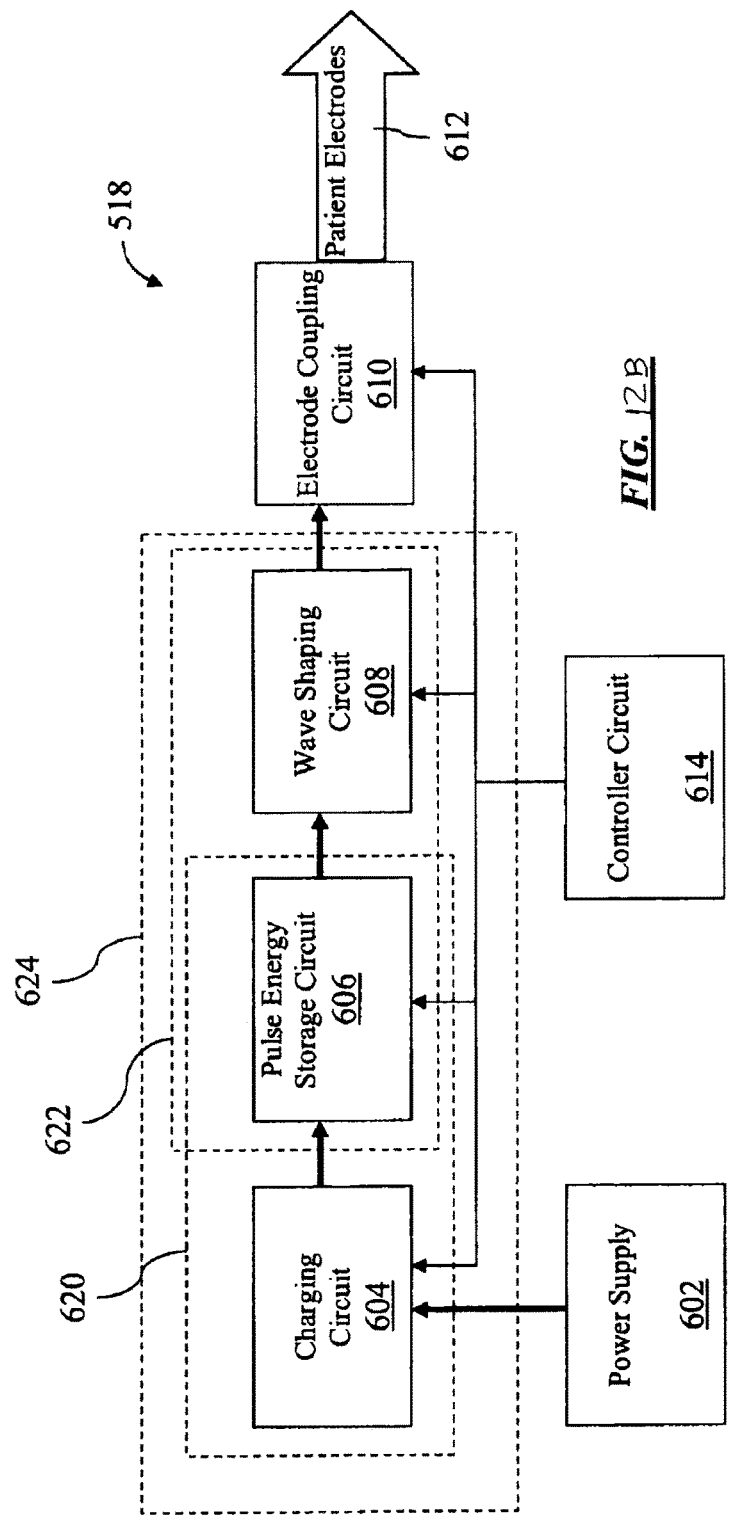

Referring now to FIGS. 12A and 12B, a detailed description of the construction of an embodiment of the three-stage ventricular cardioversion/defibrillation system is described. In the example embodiment depicted in FIG. 12A at a high level, a ventricular arrhythmia treatment apparatus 500 includes a plurality of electrodes 502 adapted to be implanted proximate a ventricle of a heart of a patient to deliver far field pulses and a plurality of electrodes 504 adapted to implanted proximate the ventricle of the heart of the patient to deliver near field pulses and sense cardiac signals. The housing of apparatus 500 can serve as one of the far-field electrodes 502 or near-field electrodes 504. Additionally, far-field electrodes 502 and near-field electrodes 504 can share at least one common electrode in some embodiments. An implantable therapy generator 506 is operably connected to the electrodes and includes a battery system 508 (or other suitable on-board energy source such as super capacitors, for example) and one or more power supply circuits 510 operably coupled and providing power to sensing circuitry 512, detection circuitry 514, control circuitry 516 and therapy circuitry 518 of the implantable therapy generator. In one type of embodiment, therapy circuitry 518 includes a specialized power supply that is fed directly from battery system 508, bypassing power supply circuitry 510. Sensing circuitry 512 senses cardiac signals representative of ventricular activity. Detection circuitry 514 evaluates the cardiac signals representative of ventricular activity to determine a ventricular cycle length and detect a ventricular arrhythmia based at least in part on the ventricular cycle length. Control circuitry 516, in response to the ventricular arrhythmia, controls generation and selective delivery of a three-stage ventricular therapy to electrodes 502 and 504, with each stage having an inter-stage delay of 50 to 800. In various embodiments, detection circuitry 514, control circuitry 516 and therapy circuitry 518 can share components. For example, in one embodiment, a common microcontroller can be a part of detection circuitry 514, control circuitry 516 and therapy circuitry 518.

The therapy circuitry 518 is operably connected to electrodes 502 and 504 and control circuitry 516. FIG. 12B illustrates an example arrangement of therapy circuitry 518 according to one type of embodiment. Therapy circuitry 518 can include its own power supply circuit 602, which is fed from battery system 508. Power supply circuit 602 can be a simple voltage regulator, or it can be a current limiting circuit that functions to prevent therapy circuitry (which has the greatest power demands of all the circuitry in the device) from drawing too much power and, consequently, causing a drop in the supply voltage below a sufficient level to power the controller and other critical components. Alternatively, power supply circuit 602 can be implemented in power supply circuit 510; or, in one type of embodiment, power supply circuit 602 can be omitted entirely, such that charging circuit 604 is fed directly from battery system 508.

Charging circuit 604 is a voltage converter circuit that produces voltages at the levels needed for the stimulation waveform. The input to charging circuit is a voltage at or near the voltage of battery system 508, which in one embodiment is between 3 and 12 volts. Since the stimulation waveform, particularly the first stage, is at a much higher voltage, up to around 100 volts, a boosting topology is used for charging circuit 604. Any suitable boosting circuit may be employed to this end, including a switching regulator utilizing one or more inductive elements (e.g., transformer, inductor, etc.), or a switching regulator utilizing capacitive elements (e.g., charge pump).

Figure 13A:
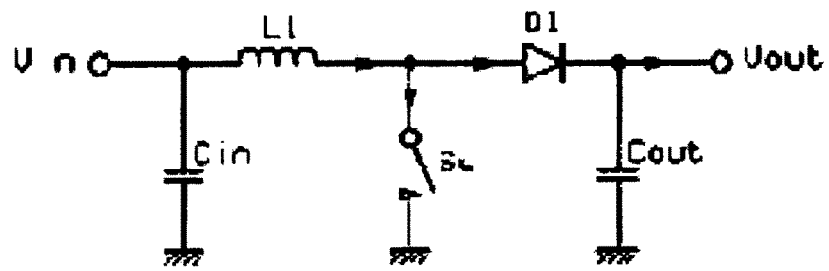
FIGS. 13A-13H depict various portions of the therapy circuitry of the device of FIGS. 12A and 12B, in greater detail, according to various embodiments.

FIGS. 13A-13F illustrate various known topologies for voltage boosting circuits that can be utilized as part of charging circuit 604 according to various embodiments. FIG. 13A illustrates a basic boost converter topology. The boost converter of FIG. 20A utilizes a single inductor indicated at L1 to store energy in each cycle of switch SW. When switch SW closes, inductor L1 is energized and develops a self-induced magnetic field. When switch SW opens, the voltage at the L1-SW-D1 node is boosted as the magnetic field in inductor L1 collapses. The associated current passes through blocking diode D1 and charges energy storage capacitor $C_{out}$ to a voltage greater than input voltage $V_{in}$.

Figure 13B:
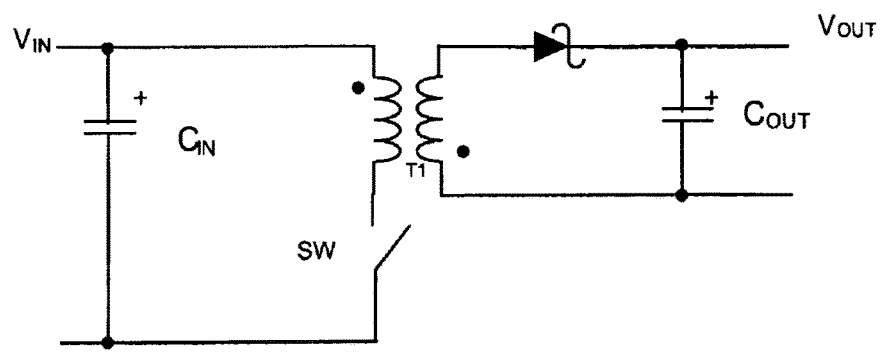

FIG. 13B illustrates a flyback converter topology. The flyback converter utilizes transformer T1 as an energy storage device as well as a step-up transformer. When switch SW is closed, the primary coil of transformer T1 is energized in similar fashion to inductor L1 of FIG. 13A. When switch SW opens, the voltage across the primary coil is reversed and boosted due to the collapsing magnetic field in the primary. The changing voltages of the primary coil are magnetically coupled to the secondary coil, which typically has a greater number of windings to further step-up the voltage on the secondary side. A typical turns ratio for defibrillator signal applications in certain embodiments is Np:Ns of about 1:15, where Np is the number of primary turns and Ns is the number of secondary turns. The high voltage across the secondary coil is rectified by the diode and stored in capacitor $C_{out}$.

Figure 13C:
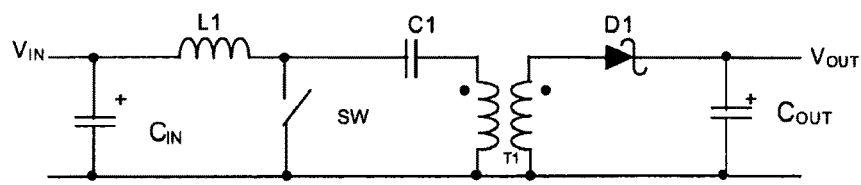

FIG. 13C illustrates a single ended primary inductance converter ("SEPIC"), which offers certain advantages over other power converter topologies. For instance, the SEPIC converter offers an advantage of not requiring significant energy storage in the transformer. Since most of the energy in a transformer is stored in its gap, this reduces the gap length requirement for the transformer. Battery voltage is applied at VIN and the switching element is switched at a fixed frequency and a duty cycle that is varied according to feedback of battery current into the power converter and output voltage. Voltage from the output of the step up transformer (T1) is rectified by the diode D1 to generate output voltage on $C_{out}$.

Figure 13D:
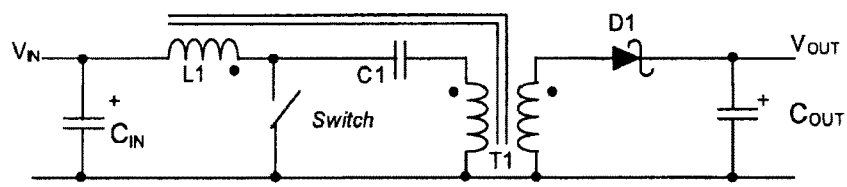

FIG. 13D illustrates a variation of the SEPIC converter of FIG. 13C. The SEPIC topology of FIG. 13D has an additional inductive component (L1). The additional inductor L1 can be implemented either discretely, or can be magnetically coupled with the high voltage transformer into a single magnetic structure, as depicted in FIG. 13D.

Figure 13E:
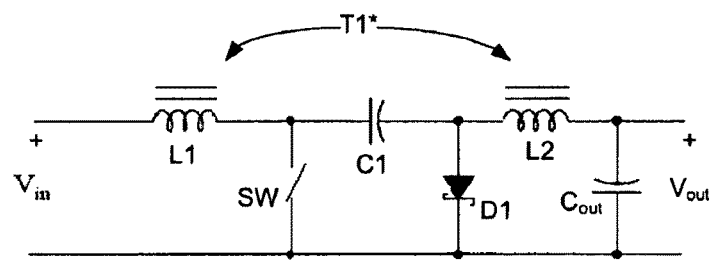

FIG. 13E illustrates a Cuk converter topology. A Cuk converter comprises two inductors, L1 and L2, two capacitors, C1 and $C_{out}$, switch SW, and diode D1. Capacitor C is used to transfer energy and is connected alternately to the input and to the output of the converter via the commutation of the transistor and the diode. The two inductors L1 and L2 are used to convert, respectively, the input voltage source ($V_1$) and the output voltage at capacitor $C_{out}$ into current sources. Similarly to the voltage converter circuits described above, the ratio of output voltage to input voltage is related to the duty cycling of switch SW. Optionally, inductors L1 and L2 can be magnetically coupled as indicated T1*.

Figure 13F:
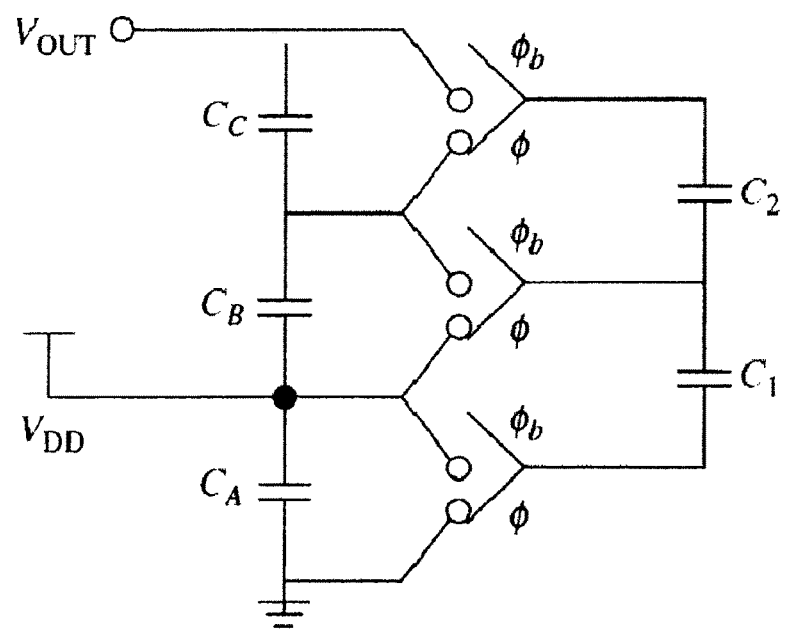

FIG. 13F illustrates a basic charge pump topology for multiplying the input voltage. The example shown is a Cockcroft-Walton multiplying circuit. Three capacitors ($C_A$, $C_B$, and $C_c$), each of capacity C, are connected in series, and capacitor $C_A$ is connected to the supply voltage, $V_{DD}$. During phase φ, capacitor $C_1$ is connected to $C_A$ and charged to voltage $V_{DD}$.

When the switches change position during the next cycle, $φ_b$, capacitor $C_1$ will share its charge with capacitor $C_B$, and both will be charged to $V_{DD}/2$ if they have equal capacity. In the next cycle, $C_2$ and $C_B$ will be connected and share a potential of $V_{DD}/4$, while $C_1$ is once again charged to $V_{DD}$. As this process continues for a few cycles, charge will be transferred to all the capacitors until a potential of $3V_{DD}$ is developed across the output Vout. Additional stages may be added to increase the voltage multiplication.

Figure 13G:
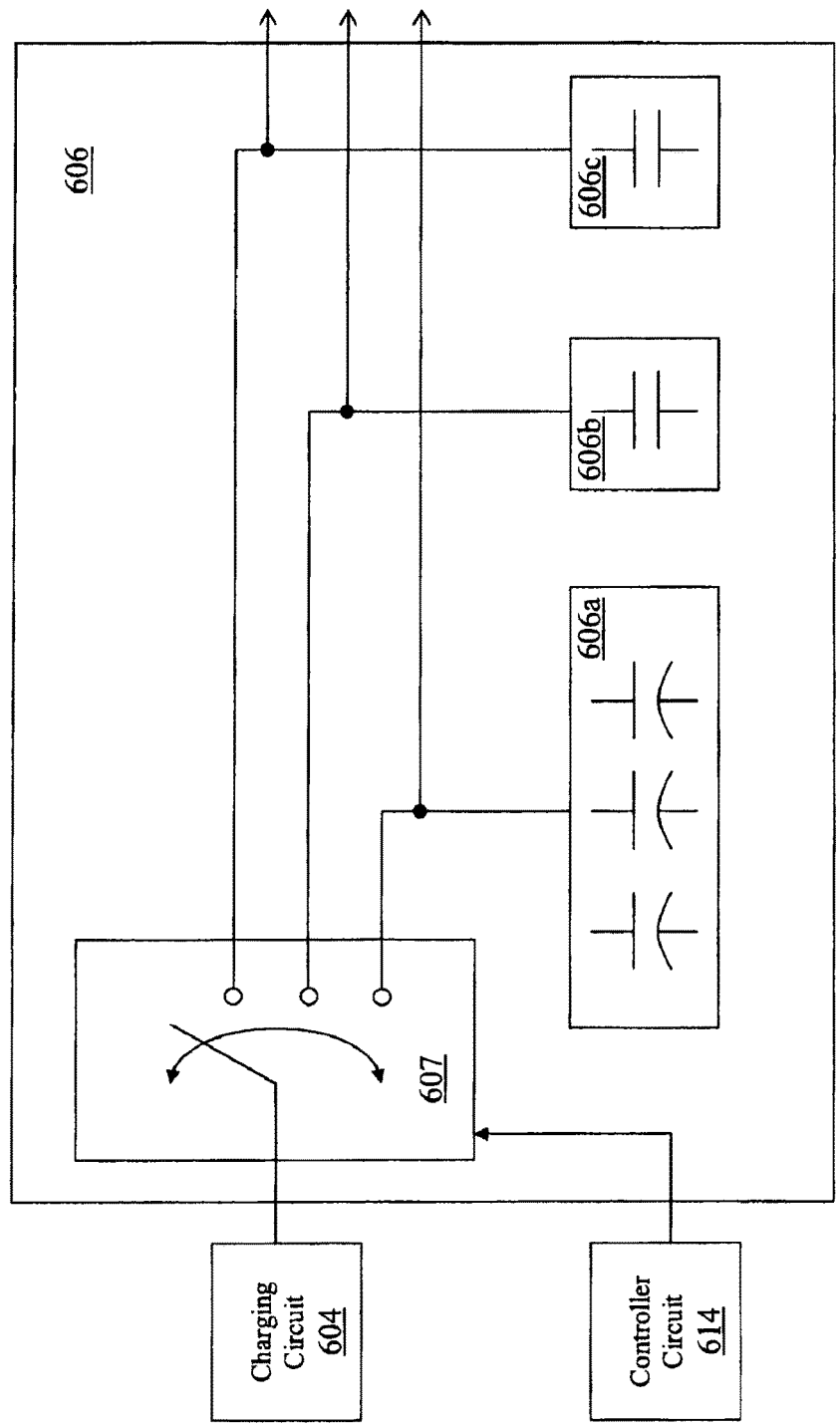
Figure 13H:
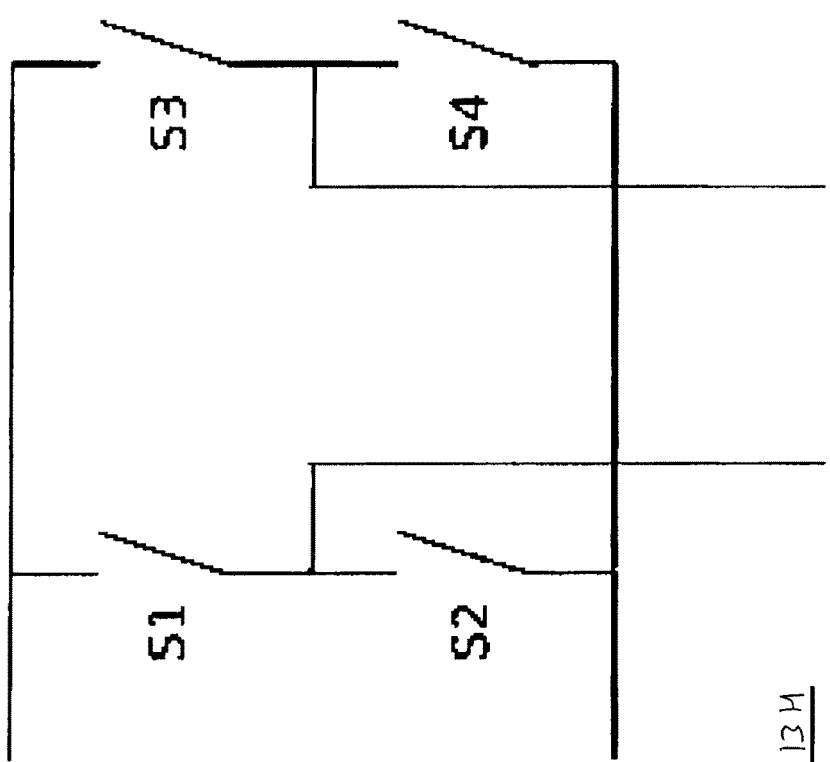

Referring again to FIG. 12B, pulse energy storage circuit 606 can take various forms. Generally, pulse energy storage circuit has energy storage capacity sufficient to store either all three stages of the ventricular therapy, or a portion of the therapy's energy, provided that the arrangement of energy storage circuit 606 and charging circuit 604 supports the ability to re-charge portions of the energy storage circuit 606 while other portions thereof are discharging or are about to discharge during application of the electrotherapy. FIG. 13G illustrates a basic example of energy storage circuit 606, in which there are three separate storage reservoirs for each of the three stages of the electrotherapy. Storage reservoir 606a stores the energy for the first stage; storage reservoir 606b for the second; and 606c for the third. Each storage reservoir can have one, or a plurality of storage elements. In one type of embodiment, each storage reservoir has a plurality of storage element groups, with each storage element group individually switchably selectable for charging and discharging. The storage elements can take any suitable form, including capacitors of a suitable technology, e.g., electrolytic, tantalum film, ceramic chip, supercap, or the like.

Storage reservoirs 606a-606c are coupled to charging circuit 604 via selector switch 607. Selector switch 607 can be implemented with a analog multiplexer, transmission gates, or any other suitable electronic switching arrangement. Selector switch 607 is controlled by controller circuit 614 in this example.

Referring again to FIG. 12B, wave shaping circuit 608 regulates the application of the electrotherapy by selecting, and controlling the discharging of the energy stored in energy storage circuit 606. In one embodiment, wave shaping circuit 608 is in the form of a H-bridge topology, as illustrated in FIG. 13G. Switches S1-S4 are individually controlled by controller circuit 614. The H-bridge topology facilitates steering, or reversing the polarity, of the electrotherapy signals, enabling a biphasic shock to be applied from a single-polarity energy storage reservoir. Other forms of switchable coupling are also contemplated for other embodiments. For instance, a set of analog transmission gates can be used, such that each storage reservoir 606a-606c is individually selectable. In this latter example, separate capacitors of opposite polarity are used for storing the charge for each phase of the biphasic unpinning waveform of the first electrotherapy phase.

Referring again to FIG. 12B, electrode coupling circuit 610 operates to select which of the multiple sets of patient electrodes 612 are coupled to the output of the wave shaping circuit 608. Electrode coupling circuit 610 can be implemented in one example embodiment using a set of analog multiplexers that are controlled by controller circuit 614.

In various other embodiments, the functionality of charging circuit 604 and pulse energy storage circuit 606 can be combined into a single circuit 620, such as a charge pump arrangement, in which certain ones of the capacitors are also used for both, building up charge, and storing the pulse energy for the electrotherapy. In another variation, the pulse energy storage circuit 606 can be one and the same circuit, as the wave shaping circuit 608, depicted at 622, such as, for example, where multiple different capacitors are used to store each individual pulse, and where the electrode coupling circuit has the capability to individually select which capacitors are switched in to which electrodes. Moreover, in yet another variation, charging circuit 604, pulse energy storage circuit 606, and wave shaping circuit 608 can be combined as a single circuit implementation 624, which can be implemented as a combination of circuits 620 and 622.

Figure 14:
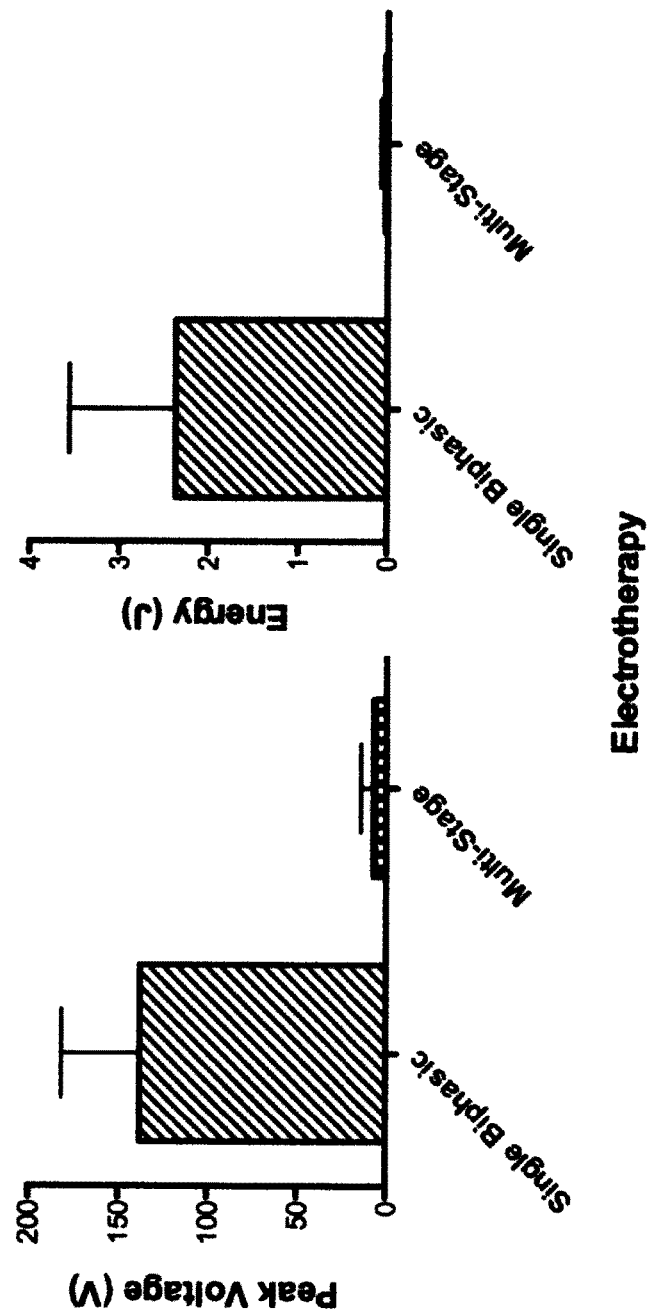
FIG. 14 depicts a sample comparison of voltage and energy ventricular defibrillation thresholds of a single-biphasic shock and the three-stage therapy of FIG. 4.

Referring to FIG. 14, results of an experimental application of the three-stage ventricular therapy as administered in a clinical study are depicted.

Two vectors to defibrillate ventricular tachyarrhythmias in canines using multiple stage electrotherapy were studied. The two vectors were (i) RV to CS and (ii) RV to left ventricular epicardial patch (LVP). As depicted in FIG. 14, multiple-stage electrotherapy delivered from the RV-CS vector significantly reduced the defibrillation threshold compared to a single biphasic shock with respect to total energy.

As described above, current implantable defibrillators use a high-energy biphasic (BP) shock to terminate ventricular tachycardia (VT) when anti-tachycardia pacing (ATP) fails. In this study, a three-stage electrotherapy as described above, was compared to a single biphasic shock, delivered via a fully endocardial lead system (refer also to FIGS. 1A and 1B).

Myocardial infarction was induced in mongrel dogs (n=3). Four days later, endocardial bipolar pace/shock leads were placed in the right ventricle (RV) apex and coronary sinus (CS). A patch (LVP) was placed over the posterolateral left ventricle. ATP (8 pulses, 88% of the VT cycle length (CL)) were administered via the RV bipole after sustained VT induction. If ATP failed, cardioversion thresholds (CVT) of the three-stage and single biphasic shock were measured. The three-stage therapy consisted of sequentially administering first stage (400), second stage (402), and third stage (404) as follows: three monophasic shock pulses delivered within one VT CL (first stage); six monophasic shock pulses delivered with an interval of 88% of the VT CL at the ventricular capture voltage (second stage), and ATP (third stage). RV-CS coil and RV-LVP shock vectors were compared.

Results indicated that the average CL of sustained VT was 148±26 ms. The success rate of ATP alone was 7.04%. The RV-CS shock vector had lower impedance than RV-LVP (54.4±18.1 Ohms versus 109.8±16.9 Ohms, respectively, p<0.001). The three-stage therapy delivered from the RV-CS vector significantly reduced the CVT compared to a single biphasic shock with respect to total energy (0.03±0.05 J versus 2.37±1.20 J, respectively, p<0.001) and peak shock voltage (7.2±6.9 V versus 137.7±43.8 V, respectively, p<0.001).

Consequently, the three-stage electrotherapy terminated ATP-resistant VT with significantly lower peak voltage and total energy compared to a conventional single biphasic shock. As such, this novel electrotherapy provides a low-voltage, low-energy alternative to high-energy ICD shocks when ATP fails, and can be delivered through a fully implantable endocardial lead system. Further, this therapy may enable device-based painless ventricular defibrillation by defibrillating at thresholds below the human pain threshold.

The embodiments above are intended to be illustrative and not limiting. Additional embodiments are within the claims. In addition, although aspects of the present invention have been described with reference to particular embodiments, those skilled in the art will recognize that changes can be made in form and detail without departing from the spirit and scope of the invention, as defined by the claims.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

The invention claimed is:

1. An implantable therapy generator, comprising:
    detection circuitry configured to detect a ventricular arrhythmia;
    control circuitry operably connected to the detection circuitry that, in response to detection of a ventricular arrhythmia, controls generation and selective delivery of a therapy without confirmation of conversion of the ventricular arrhythmia during the therapy, the therapy including:
        a first set of electrical pulses to destabilize a reentry associated with the ventricular arrhythmia; and
        a second set of electrical pulses to terminate the reentry associated with the ventricular arrhythmia, wherein the first set of pulses is greater in number than the second set of pulses.

2. The implantable therapy generator of claim 1, further comprising:
    at least one far field implantable electrode to deliver at least one of the first and second sets of electrical pulses.

3. The implantable therapy generator of claim 1, further comprising:
    at least one far field implantable electrode to deliver the first set of pulses; and
    at least one near field implantable electrode to deliver the second set of pulses.

4. The implantable therapy generator of claim 3, wherein the first set of electrical pulses have a voltage lower than the second set of electrical pulses.

5. The implantable therapy generator of claim 1, further comprising:

at least one near field implantable electrode to deliver the first set of pulses; and
at least one far field implantable electrode to deliver the second set of pulses.

6. The implantable therapy generator of claim 1, further comprising:
at least one near field implantable electrode to deliver at least one of the first and second sets of electrical pulses.

7. The implantable therapy generator of claim 1, wherein each electrical pulse of the first set of pulses includes at least one parameter configured to destabilize the reentry.

8. The implantable therapy generator of claim 1, wherein each electrical pulse of the first set of pulses is delivered according to at least one parameter configured to destabilize the reentry.

9. The implantable therapy generator of claim 1, wherein each electrical pulse of the second set of electrical pulses includes at least one parameter configured to terminate the reentry.

10. The implantable therapy generator of claim 1, wherein each electrical pulse of the second set of pulses is delivered according to at least one parameter configured to terminate the reentry.

11. The implantable therapy generator of claim 1, wherein the therapy further includes a delay separating the first set of pulses and the second set of pulses.

12. The implantable therapy generator of claim 11, wherein the delay is greater than a duration of the first set of pulses and greater than a duration of the second set of pulses.

13. The implantable therapy generator of claim 11, wherein the delay has a predetermined duration.

14. An implantable therapy generator, comprising:
detection circuitry configured to detect a ventricular arrhythmia;
control circuitry operably connected to the detection circuitry that, in response to detection of a ventricular arrhythmia, controls generation and selective delivery of a therapy without confirmation of conversion of the ventricular arrhythmia during the therapy, the therapy including:
a first set of electrical pulses to destabilize a reentry associated with the ventricular arrhythmia; and
a second set of electrical pulses to terminate the reentry associated with the ventricular arrhythmia, wherein the second set of pulses is greater in number than the first set of pulses.

15. The implantable therapy generator of claim 14, further comprising:
at least one far field implantable electrode to deliver at least one of the first and second sets of electrical pulses.

16. The implantable therapy generator of claim 14, further comprising:
at least one far field implantable electrode to deliver the first set of pulses; and
at least one near field implantable electrode to deliver the second set of pulses.

17. The implantable therapy generator of claim 16, wherein the first set of electrical pulses have a voltage lower than the second set of electrical pulses.

18. The implantable therapy generator of claim 14, further comprising:
at least one near field implantable electrode to deliver the first set of pulses; and
at least one far field implantable electrode to deliver the second set of pulses.

19. The implantable therapy generator of claim 14, further comprising:
at least one near field implantable electrode to deliver at least one of the first and second sets of electrical pulses.

20. The implantable therapy generator of claim 14, wherein each electrical pulse of the first set of pulses includes at least one parameter configured to destabilize the reentry.

21. The implantable therapy generator of claim 14, wherein each electrical pulse of the first set of pulses is delivered according to at least one parameter configured to destabilize the reentry.

22. The implantable therapy generator of claim 14, wherein each electrical pulse of the second set of electrical pulses includes at least one parameter configured to terminate the reentry.

23. The implantable therapy generator of claim 14, wherein each electrical pulse of the second set of pulses is delivered according to at least one parameter configured to terminate the reentry.

24. The implantable therapy generator of claim 14, wherein the therapy further includes a delay separating the first set of pulses and the second set of pulses.

25. The implantable therapy generator of claim 24, wherein the delay is greater than a duration of the first set of pulses and greater than a duration of the second set of pulses.

26. The implantable therapy generator of claim 24, wherein the delay has a predetermined duration.

27. A method for treating a ventricular arrhythmia, the method comprising:
detecting a ventricular arrhythmia with an implantable electrical stimulator, the implantable electrical stimulator operably coupled to at least one electrode implantable proximate a heart of a patient, the implantable electrical stimulator including:
detection circuitry configured to evaluate at least one biological signal to detect the ventricular arrhythmia, wherein the at least one biological signal corresponds to electrical activity of the heart; and
control circuitry configured to deliver a plurality of sets of electrical stimulation to the heart in response to the detected ventricular arrhythmia, the plurality of sets of electrical stimulation having at least a first set and a second set, wherein the first set includes a first plurality of pulses and is configured to destabilize a reentry associated with the ventricular arrhythmia, and wherein the second set includes a second plurality of pulses and is configured to terminate the reentry associated with the ventricular arrhythmia, wherein the first plurality of pulses in the first set is greater in number than the second plurality of pulses in the second set; and
delivering the plurality of sets of electrical stimulation without confirmation of conversion of the detected ventricular arrhythmia during delivery of the plurality of sets of electrical stimulation.

28. The method of claim 27, wherein at least one of the first and second sets of electrical stimulation are delivered from at least one far field implantable electrode.

29. The method of claim 27, wherein the first set of electrical stimulation is delivered from at least one far field implantable electrode, and wherein the second set of electrical stimulation is delivered from at least one near field implantable electrode.

30. The method of claim 29, wherein the first set of electrical pulses have a voltage lower than the second set of electrical pulses.

31. The method of claim 27, wherein the first set of electrical stimulation is delivered from at least one near field implantable electrode, and wherein the second set of electrical stimulation is delivered from at least one far field implantable electrode.

32. The method of claim 27, wherein at least one of the first and second sets of electrical stimulation are delivered from at least one near field implantable electrode.

33. The method of claim 27, wherein each electrical pulse of the first set of pulses includes at least one parameter configured to destabilize the reentry.

34. The method of claim 27, wherein each electrical pulse of the first set of pulses is delivered according to at least one parameter configured to destabilize the reentry.

35. The method of claim 27, wherein each electrical pulse of the second set of electrical pulses includes at least one parameter configured to terminate the reentry.

36. The method of claim 27, wherein each electrical pulse of the second set of pulses is delivered according to at least one parameter configured to terminate the reentry.

37. The method of claim 27, wherein the first set and the second set are separated by a delay.

38. The method of claim 37, wherein the delay between the first and second sets is greater than a duration of the first set and greater than a duration of the second set.

39. The method of claim 37, wherein the delay has a predetermined duration.

40. A method for treating a ventricular arrhythmia, the method comprising:
    detecting a ventricular arrhythmia with an implantable electrical stimulator, the implantable electrical stimulator operably coupled to at least one electrode implantable proximate a heart of a patient, the implantable electrical stimulator including:
        detection circuitry configured to evaluate at least one biological signal to detect the ventricular arrhythmia, wherein the at least one biological signal corresponds to electrical activity of the heart; and
        control circuitry configured to deliver a plurality of sets of electrical stimulation to the heart in response to the detected ventricular arrhythmia, the plurality of sets of electrical stimulation having at least a first set and a second set, wherein the first set includes a first plurality of pulses and is configured to destabilize a reentry associated with the ventricular arrhythmia, and wherein the second set includes a second plurality of pulses and is configured to terminate the reentry associated with the ventricular arrhythmia, wherein the second plurality of pulses in the second se is greater in number than the first plurality of pulses in the first set; and
    delivering the plurality of sets of electrical stimulation without confirmation of conversion of the detected ventricular arrhythmia during delivery of the plurality of sets of electrical stimulation.

41. The method of claim 40, wherein at least one of the first and second sets of electrical stimulation are delivered from at least one far field implantable electrode.

42. The method of claim 40, wherein the first set of electrical stimulation is delivered from at least one far field implantable electrode, and wherein the second se of electrical stimulation is delivered from at least one near field implantable electrode.

43. The method of claim 42, wherein the first set of electrical pulses have a voltage lower than the second set of electrical pulses.

44. The method of claim 40, wherein the first set of electrical stimulation is delivered from at least one near field implantable electrode, and wherein the second set of electrical stimulation is delivered from at least one far field implantable electrode.

45. The method of claim 40, wherein at least one of the first and second sets of electrical stimulation are delivered from at least one near field implantable electrode.

46. The method of claim 40, wherein each electrical pulse of the first set of pulses includes at least one parameter configured to destabilize the reentry.

47. The method of claim 40, wherein each electrical pulse of the first set of pulses is delivered according to at least one parameter configured to destabilize the reentry.

48. The method of claim 40, wherein each electrical pulse of the second set of electrical pulses includes at least one parameter configured to terminate the reentry.

49. The method of claim 40, wherein each electrical pulse of the second set of pulses is delivered according to at least one parameter configured to terminate the reentry.

50. The method of claim 40, wherein the first set and the second set are separated by a delay.

51. The method of claim 50, wherein the delay between the first and second sets is greater than a duration of the first se and greater than a duration of the second set.

52. The method of claim 50, wherein the delay has a predetermined duration.

* * * * *

UNITED STATES PATENT AND TRADEMARK OFFICE
CERTIFICATE OF CORRECTION

PATENT NO. : 10,099,062 B2
APPLICATION NO. : 15/367927
DATED : October 16, 2018
INVENTOR(S) : Igor R. Efimov, Wenwen Li and Ajit H. Janardhan It is certified that error appears in the above-identified patent and that said Letters Patent is hereby corrected as shown below:

In the Specification

After Column 1, Line 28, please insert the following new heading and statement:
--GOVERNMENT INTEREST
This invention was made with government support under HL067322 awarded by the National Institutes of Health. The government has certain rights in the invention.--

Signed and Sealed this
Fifth Day of March, 2019

Andrei Iancu
*Director of the United States Patent and Trademark Office*